(12) United States Patent
Altschuler

(10) Patent No.: US 12,357,465 B2
(45) Date of Patent: Jul. 15, 2025

(54) IMPLANTATION TOOL AND PROTOCOL FOR OPTIMIZED SOLID SUBSTRATES PROMOTING CELL AND TISSUE GROWTH

(71) Applicant: Cartiheal (2009) Ltd., Kfar Saba (IL)

(72) Inventor: Nir Altschuler, Tzur Yitzchak (IL)

(73) Assignee: Cartiheal (2009) Ltd., Kfar Saba (IL)

( * ) Notice: Subject to any disclaimer, the term of this patent is extended or adjusted under 35 U.S.C. 154(b) by 1233 days.

(21) Appl. No.: 16/959,447

(22) PCT Filed: Dec. 30, 2018

(86) PCT No.: PCT/IL2018/051413
§ 371 (c)(1),
(2) Date: Jul. 1, 2020

(87) PCT Pub. No.: WO2019/135216
PCT Pub. Date: Jul. 11, 2019

(65) Prior Publication Data
US 2020/0368027 A1 Nov. 26, 2020

Related U.S. Application Data

(60) Provisional application No. 62/783,221, filed on Dec. 21, 2018, provisional application No. 62/612,735, filed on Jan. 2, 2018.

(51) Int. Cl.
*A61F 2/30* (2006.01)
*A61F 2/46* (2006.01)

(52) U.S. Cl.
CPC ........ *A61F 2/30756* (2013.01); *A61F 2/4618* (2013.01); *A61F 2002/30214* (2013.01);
(Continued)

(58) Field of Classification Search
CPC ................ A61F 2/30756; A61F 2/4618; A61F 2002/2835; A61F 2002/2839;
(Continued)

(56) References Cited

U.S. PATENT DOCUMENTS 5,490,852 A 2/1996 Azer et al.
5,976,147 A 11/1999 LaSalle et al.
(Continued)

FOREIGN PATENT DOCUMENTS

KR 20180003587 A * 1/2018
WO WO-2004008943 A2 * 1/2004 ............. A61B 6/505
(Continued)

OTHER PUBLICATIONS

Histology. Cartilage, Bone & Ossification: Bone. Faculty of Biological Sciences, University of Leeds. https://www.histology.leeds.ac.uk/bone/bone.php (Year: 2023).*
(Continued)

*Primary Examiner* — Christie Bahena
(74) *Attorney, Agent, or Firm* — Seager, Tufte & Wickhem LLP

(57) ABSTRACT

This invention provides methods for optimal implantation of a solid substrate for promoting cell or tissue growth or restored function in an osteochondral, bone or cartilage tissue in a subject in need thereof. The methods include selecting and preparing a solid substrate for promoting cell or tissue growth or restored function for implantation, which solid substrate has a length and width or that promotes a tight fit within the boundaries of the implantation site and is further characterized by a height sufficient such that when a first terminus of said solid substrate is implanted within a bone in a site for implantation, a second terminus of said solid substrate is at a height at least 2 mm less than an articular cartilage layer surface or is proximal to a tide mark region in said implantation site and optionally applying a biocompatible polymer layer to an apical surface of said implant, which layer does not exceed the articular cartilage layer surface in height. Tools for implementation of optimal
(Continued)

positioning are described including a unique tool (5-120) for trimming cartilage at the implantation site.

31 Claims, 10 Drawing Sheets

(52) U.S. Cl.
CPC ............... *A61F 2002/30224* (2013.01); *A61F 2002/30253* (2013.01); *A61F 2002/30593* (2013.01); *A61F 2002/30617* (2013.01); *A61F 2002/30759* (2013.01); *A61F 2002/30761* (2013.01)

(58) Field of Classification Search
CPC . A61F 2002/30214; A61F 2002/30224; A61B 17/1637; A61B 17/3205
See application file for complete search history.

(56) References Cited

U.S. PATENT DOCUMENTS

| | | |
|---|---|---|
| 7,166,133 B2 | 1/2007 | Evans et al. |
| 7,758,643 B2 | 7/2010 | Stone et al. |
| 7,887,598 B2 | 2/2011 | Evans et al. |
| 8,790,681 B2 | 7/2014 | Altschuler et al. |
| 8,802,115 B2 | 8/2014 | Altschuler et al. |
| 9,668,754 B2 | 6/2017 | Pfeiffer et al. |
| 9,770,531 B2 | 9/2017 | Altschuler |
| 10,046,084 B2 | 8/2018 | Altschuler et al. |
| 10,080,570 B2 | 9/2018 | Pfeiffer et al. |
| 10,080,818 B2 | 9/2018 | Altschuler et al. |
| 10,271,938 B2 | 4/2019 | Altschuler |
| 10,342,897 B2 | 7/2019 | Altschuler |
| 10,702,627 B2 | 7/2020 | Altschuler |
| 10,799,251 B2 | 10/2020 | Altschuler et al. |
| 10,806,823 B2 | 10/2020 | Altschuler |
| 2003/0135217 A1 | 7/2003 | Buttermann et al. |
| 2003/0236573 A1 | 12/2003 | Evans et al. |
| 2007/0276506 A1* | 11/2007 | Troxel ................... A61F 2/28 8/94.11 |
| 2008/0249632 A1 | 10/2008 | Stone et al. |
| 2009/0024229 A1* | 1/2009 | Chen ................... A61F 2/28 623/23.72 |
| 2009/0110710 A1 | 4/2009 | Evans et al. |
| 2009/0324683 A1* | 12/2009 | Evans ................... A61L 27/54 427/2.26 |
| 2013/0006248 A1 | 1/2013 | Ellis |
| 2014/0065573 A1 | 3/2014 | Wang |
| 2014/0100665 A1* | 4/2014 | Gray ................... A61F 2/2803 623/23.48 |
| 2014/0180414 A1 | 6/2014 | Pfeiffer et al. |
| 2016/0000969 A1 | 1/2016 | Altschuler |
| 2016/0081758 A1* | 3/2016 | Bonutti ............... A61B 17/1746 606/130 |
| 2016/0175098 A1 | 6/2016 | Altschuler et al. |
| 2016/0184477 A1 | 6/2016 | Altschuler |
| 2017/0281198 A1* | 10/2017 | Pfeiffer ............... A61B 17/1615 |
| 2018/0154041 A1 | 6/2018 | Altschuler et al. |
| 2019/0053815 A1 | 2/2019 | Altschuler et al. |
| 2020/0276359 A1 | 9/2020 | Altschuler |

FOREIGN PATENT DOCUMENTS

| | | | | |
|---|---|---|---|---|
| WO | WO-2012038962 A1 * | 3/2012 | ............... | A61F 2/28 |
| WO | WO-2014125478 A1 * | 8/2014 | ............... | A61F 2/28 |
| WO | WO-2016178226 A1 * | 11/2016 | ......... | A61B 17/1604 |

OTHER PUBLICATIONS

Bonutti summary. 20160081758 (Year: 2016).*
International Search Report for PCT/IL2018/051413; I.A. fd Dec. 30, 2018, mailed Apr. 16, 2019, from the European Patent Office, Rijswijk, NL.
International Preliminary Report on Patentability (IPRP), Chapter I of the Patent Cooperation Treaty, including the Written Opinion, for PCT/IL2018/051413; I.A. fd Dec. 30, 2018, issued Jul. 7, 2020, by the International Bureau of WIPO, Geneva, Switzerland.
Office action for European Patent Application No. 18839735.0, dated Dec. 2, 2021, European Patent Office, Munich, Germany.

* cited by examiner

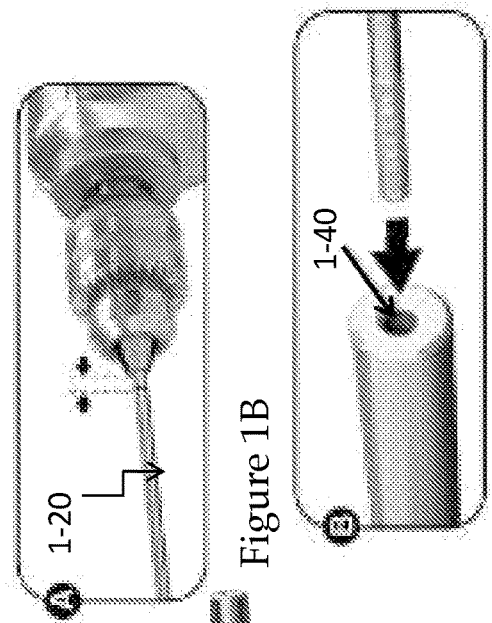
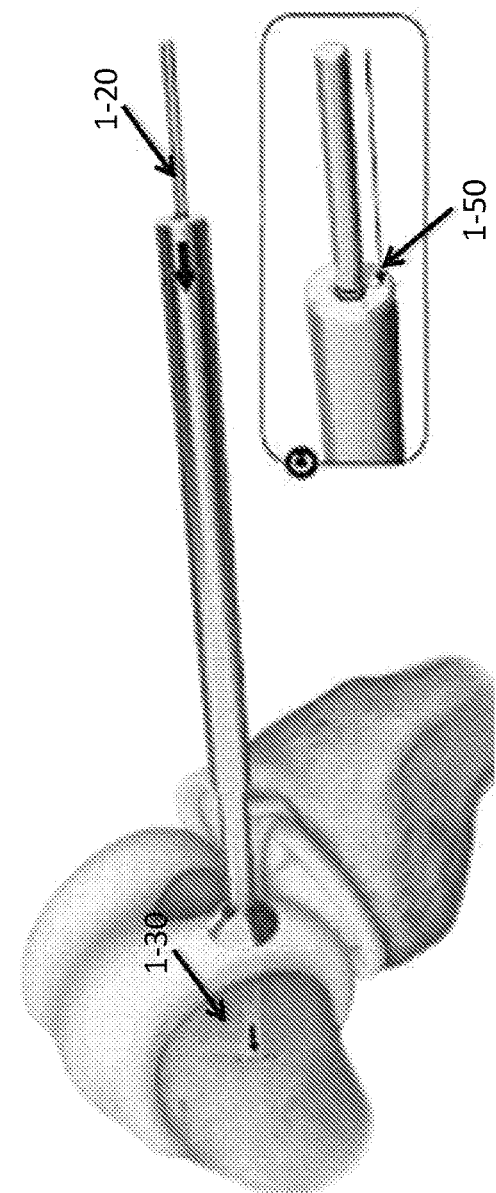
Figure 1A
Figure 1B
Figure 1C
Figure 1D
Figure 1E

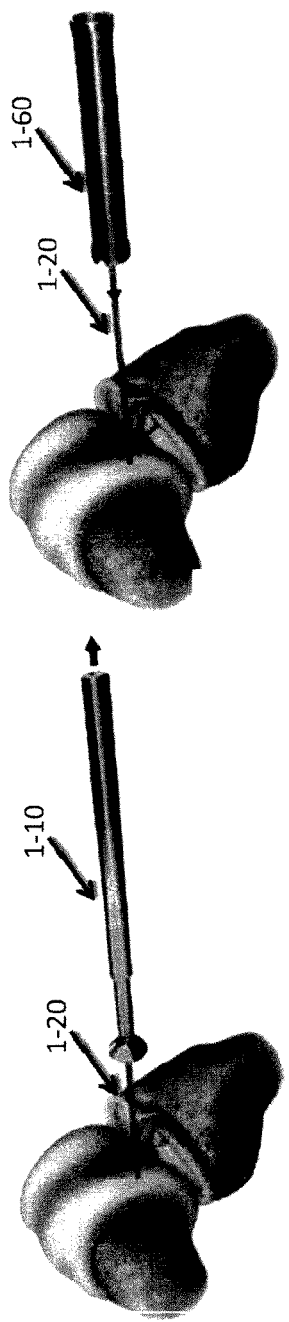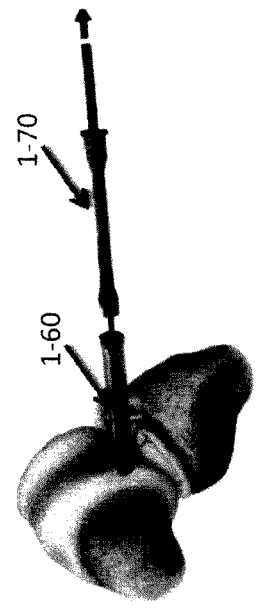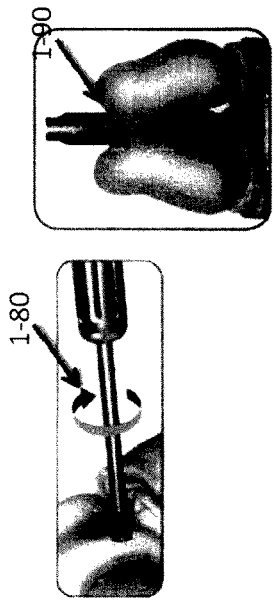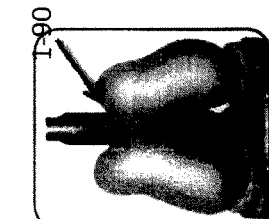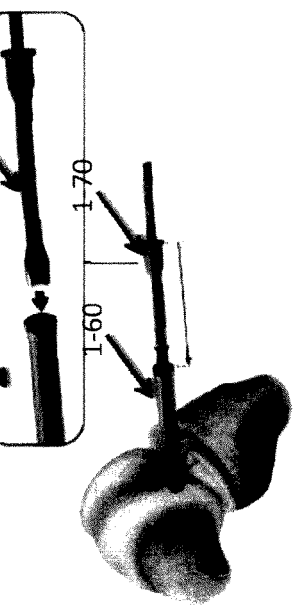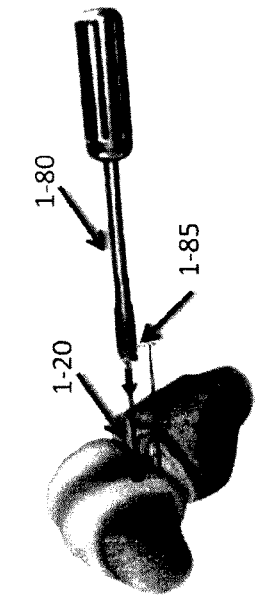
Figure 1F    Figure 1G    Figure 1I    Figure 1L
Figure 1H    Figure 1J    Figure 1K

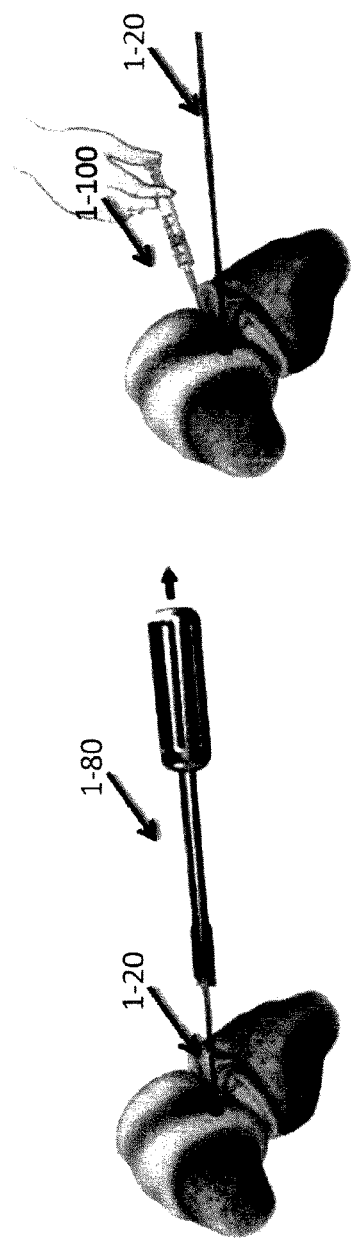
Figure 1M
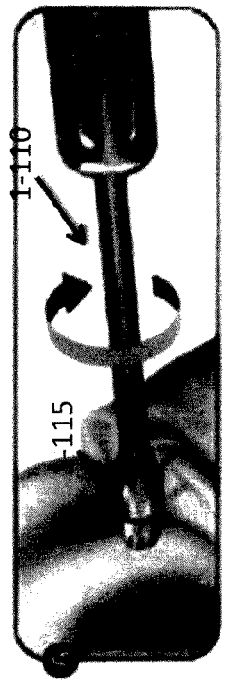
Figure 1N
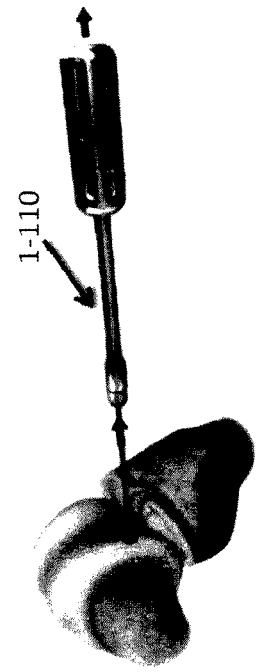
Figure 1R
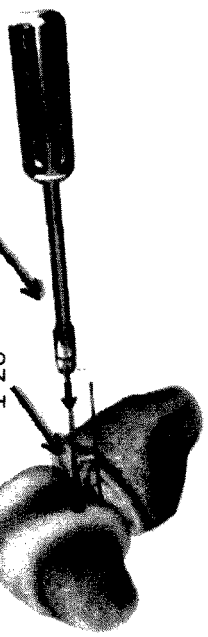
Figure 1O
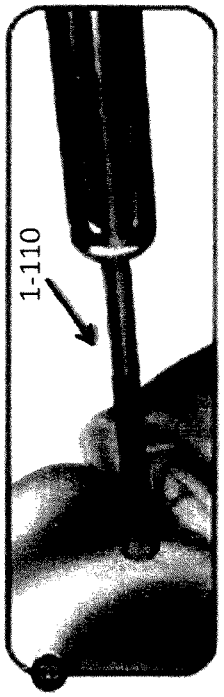
Figure 1P
Figure 1Q

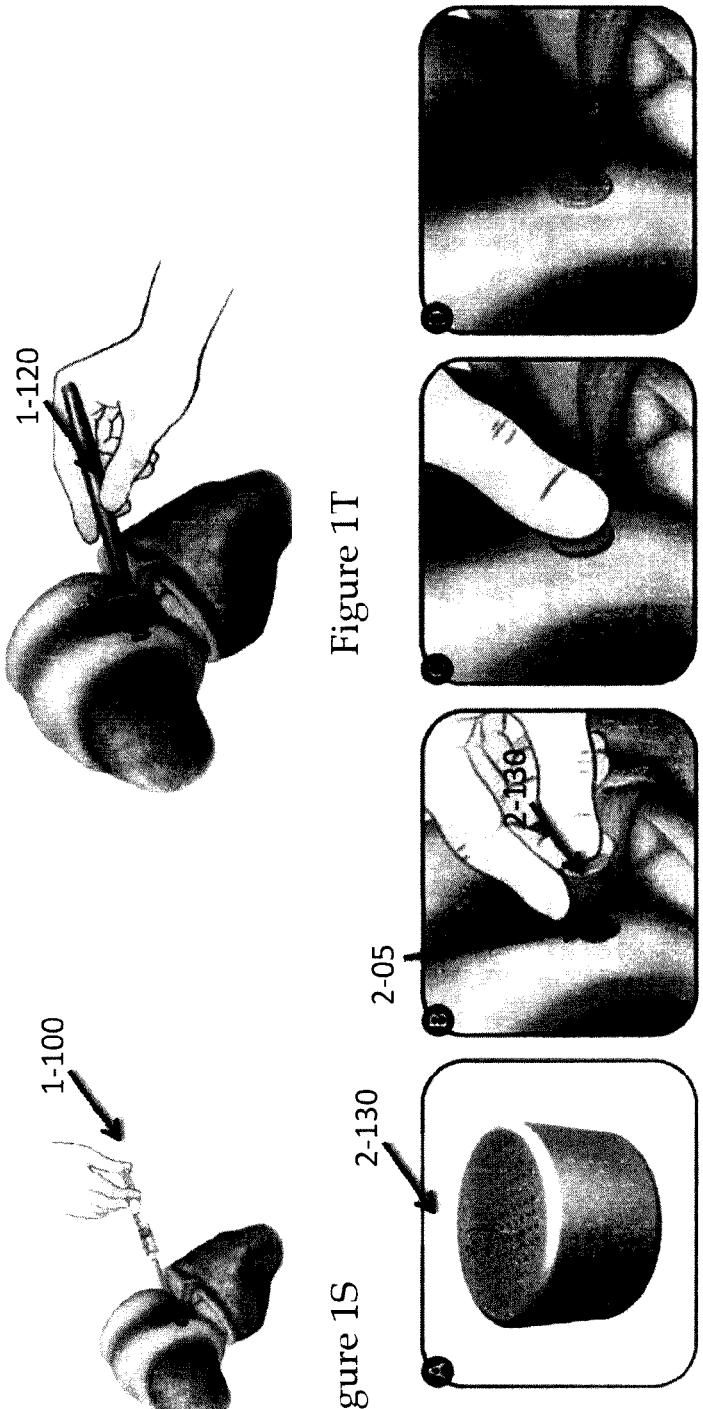
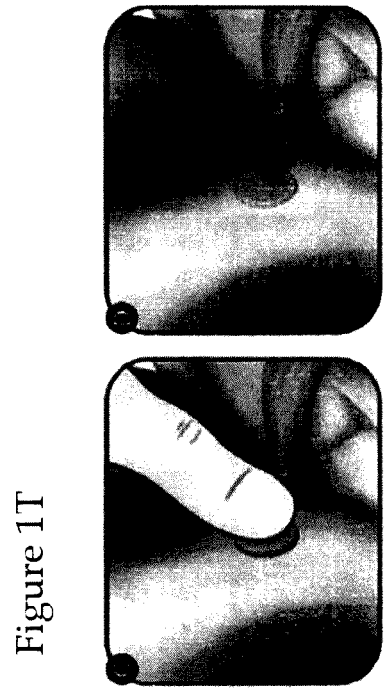
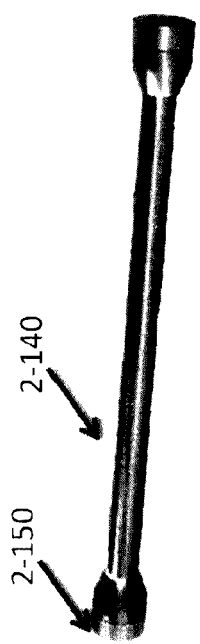
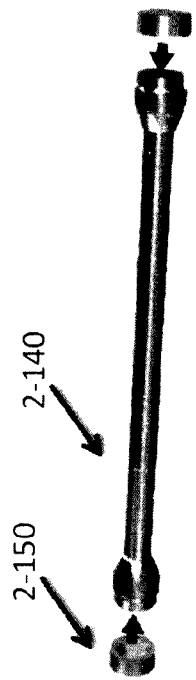

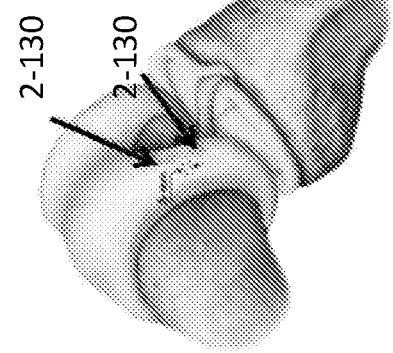
Figure 2G
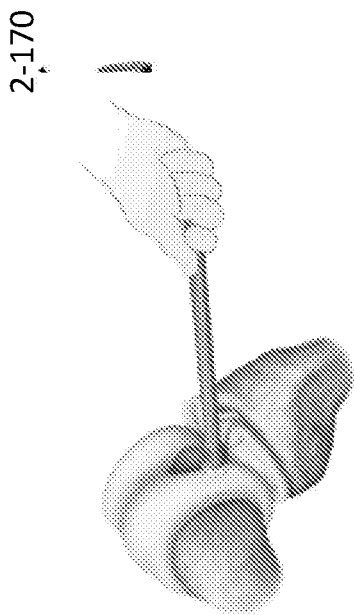
Figure 2H
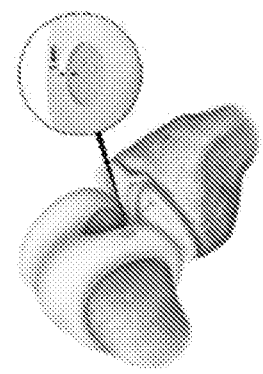
Figure 2J
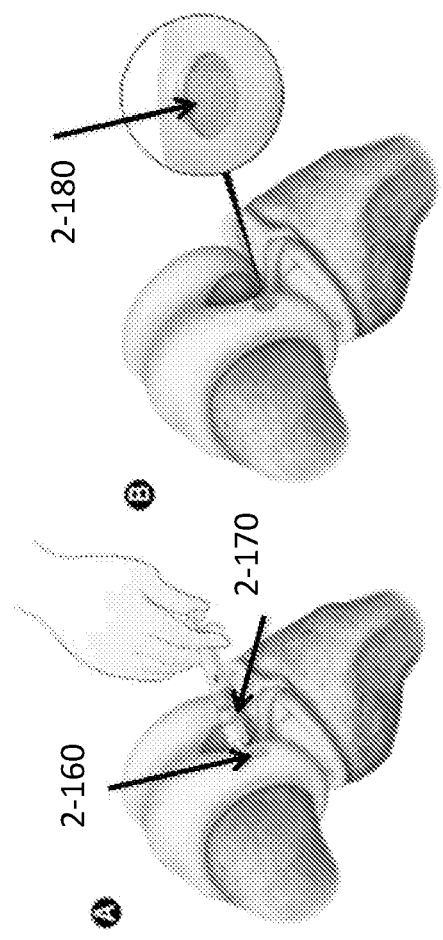
Figure 2I
Figure 2K
Figure 2L

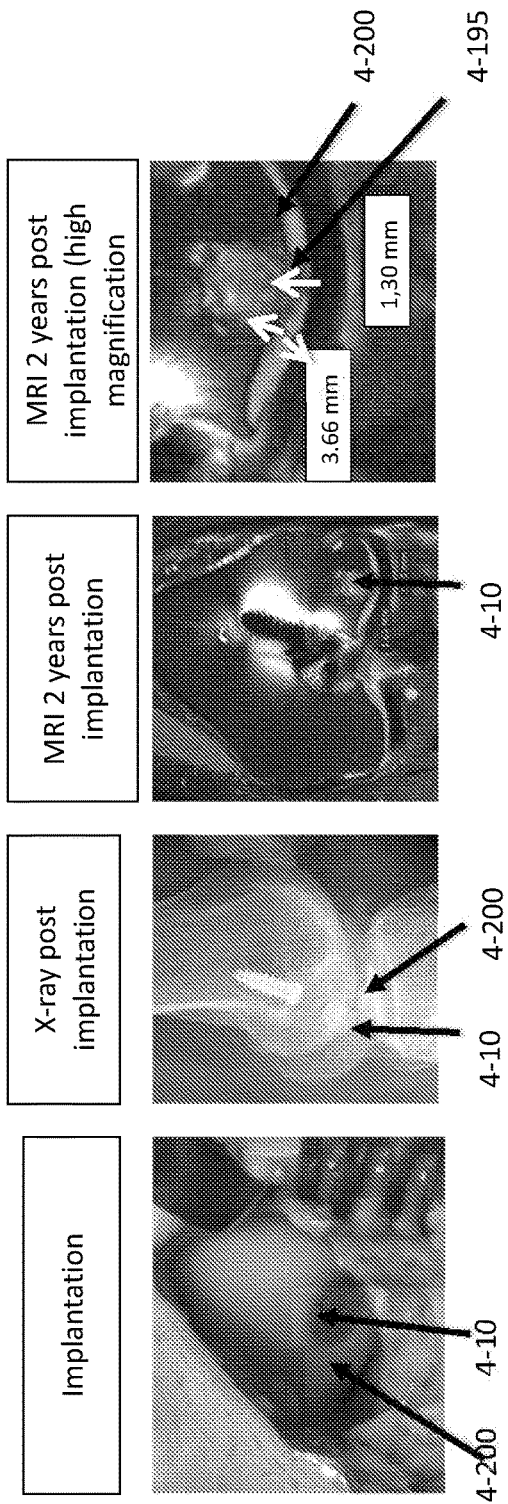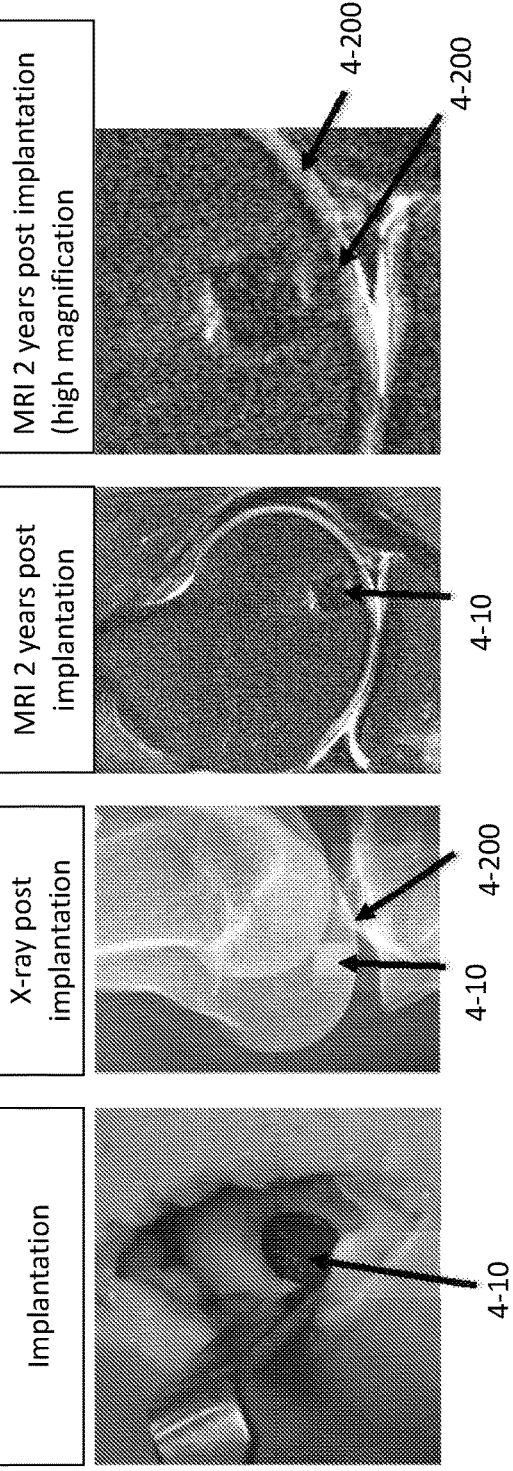
Figure 4A  Figure 4B  Figure 4C  Figure 4D
Figure 4E  Figure 4F  Figure 4G  Figure 4H

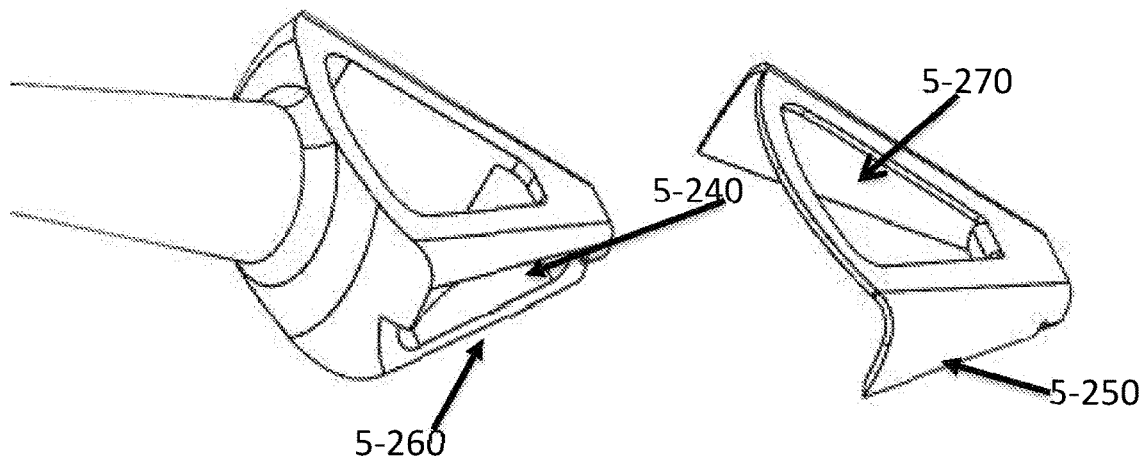
Figure 5C
Figure 5D
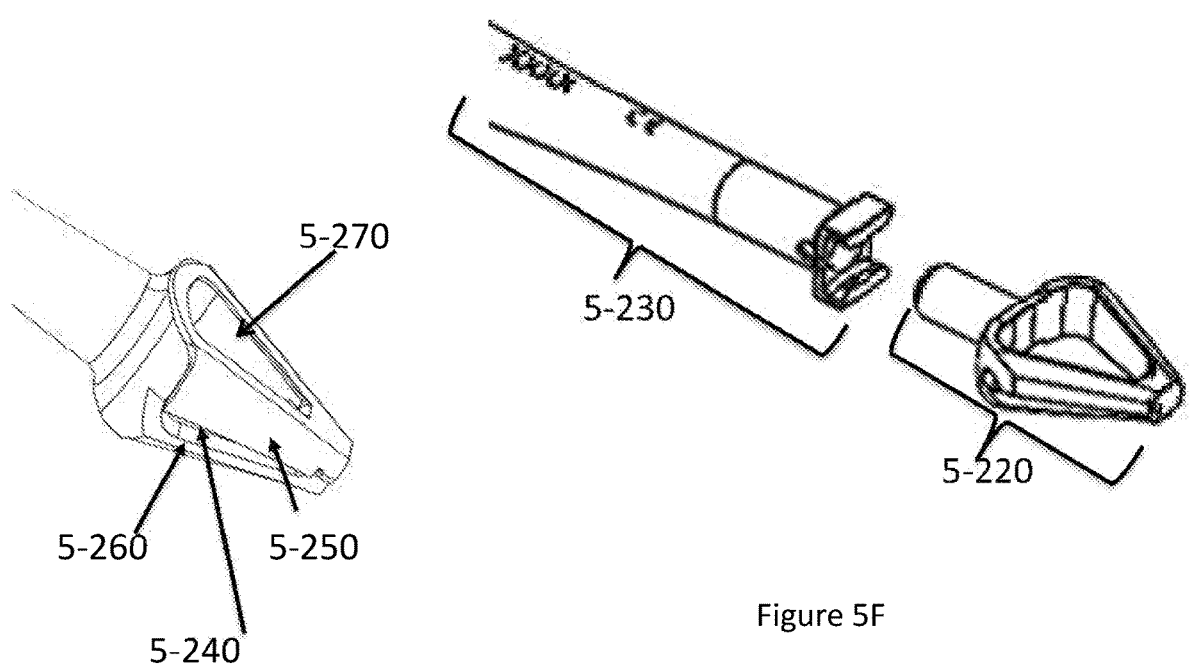
Figure 5E
Figure 5F

IMPLANTATION TOOL AND PROTOCOL FOR OPTIMIZED SOLID SUBSTRATES PROMOTING CELL AND TISSUE GROWTH

CROSS REFERENCE TO RELATED APPLICATIONS

This application claims the benefit of U.S. Provisional Patent Application No. 62/612,735 filed Jan. 2, 2018 and U.S. Provisional Patent Application No. 62/783,221 filed Dec. 21, 2018, both of which applications are hereby incorporated by reference in their entirety.

BACKGROUND OF THE INVENTION

Tissue growth, regeneration and repair are often necessary to restore function and reconstruct the morphology of the tissue, for example, as a result of exposure to trauma, neoplasia, abnormal tissue growth, aging, and others.

Articular cartilage is a highly specialized tissue that covers the surfaces of long bones to allow almost frictionless motion under large loads. In the healthy skeleton, this articulating function allows bones to change their relative angular relationship about a joint, as in the hip and the knee joints. This function of joints occurs painlessly and virtually without additional effort due to the low friction of mating joint surfaces which arises from the properties of the synovial fluid within the joint, and the smooth topography of the cartilage surfaces.

A number of diseases/conditions arise due to cartilage damage, which may range from localized tears, to focal areas of loss of coverage of the underlying bone, to degenerative conditions, such as osteo- and rheumatoid arthritis in which the entire cartilage layer and underlying (subchondral) bone can be affected. Generalized or degenerative conditions, most commonly osteoarthritis, are frequently treated with total joint replacement in which the cartilage surface and underlying bone are completely replaced with artificial materials that articulate with minimal friction.

Synthetic materials have been used as a substrate for promoting ex-vivo tissue assembly and repair, and similarly for restoring and reconstructing such tissues, for example for bone, for many years, with mixed success.

Another possibility is autologous tissue grafting, although the supply of autologous tissue is limited and its collection may be painful, with the risk of infection, hemorrhage, cosmetic disability, nerve damage, and loss of function. In addition, significant morbidity is associated with autograft harvest sites. These problems may be overcome by engineering tissue using solid substrates made of synthetic or natural biomaterials that promote the adhesion, migration, proliferation, and differentiation of stem cells, for example, mesenchymal stem cells (MSCs).

Many diseases and conditions whose treatment is sought would benefit from the ability to promote cell and tissue growth in a site-specific manner, promoting growth and incorporation of new tissue within a damaged or diseased site.

In bone and cartilage applications, the immediate microenvironment and the three-dimensional (3D) organization are important factors in differentiation in general and particularly in chondrogenic and osteogenic differentiation.

Some bone tissue engineering scaffolds consists of natural polymers, such as collagen, alginate, hyaluronic acid, and chitosan. Natural materials offer the advantages of specific cell interaction, easy seeding of cells because of their hydrophilic interactions, low toxicity and low chronic inflammatory response. However, these scaffolds often are mechanically unstable and do not readily contribute to the creation of tissue structures with a specific predefined shape for transplantation. To obtain mechanical strength, chemical modification is required, which may lead to toxicity.

Defects and degeneration of the articular cartilage surfaces of joints causes pain and stiffness. Damage to cartilage which protects joints can result from either physical injury as a result of trauma, sports or repetitive stresses (e.g., osteochondral fracture, secondary damage due to cruciate ligament injury) or from disease (e.g. osteoarthritis, rheumatoid arthritis, aseptic necrosis, osteochondritis dissecans).

Osteoarthritis (OA) results from general wear and tear of joints, most notably hip and knee joints. Osteoarthritis is common in the elderly but, in fact, by age 40 most individuals have some osteoarthitic changes in their weight bearing joints. Another emerging trend increasing the prevalence of osteoarthritis is the rise in obesity. The CDC estimates that 30% of American adults (or 60 million people) are obese. Obese adults are 4 times more likely to develop knee OA than normal weight adults Rheumatoid arthritis is an inflammatory condition which results in the destruction of cartilage. It is thought to be, at least in part, an autoimmune disease with sufferers having a genetic predisposition to the disease.

Orthopedic prevention and repair of damaged joints is a significant burden on the medical profession both in terms of expense and time spent treating patients. In part, this is because cartilage does not possess the capacity for self-repair. Attempts to re-grow hyaline cartilage for repair of cartilage defects remain unsuccessful. Orthopedic surgery is available in order to repair defects and prevent articular damage in an effort to forestall serious degenerative changes in a joint. The use of surgical techniques often requires the removal and donation of healthy tissue to replace the damaged or diseased tissue. Techniques utilizing donated tissue from autografts, allografts, or xenografts are wholly unsatisfactory as autografts add additional trauma to a subject and allografts and xenografts are limited by immunological reactivity to the host subject and possible transfer of infective agents. Surgical attempts to utilize materials other than human or animal tissue for cartilage regeneration have been unsuccessful.

As each joint is unique in terms of the geometry of its articulating surfaces, another challenge in successful grafting/implantation has been deemed the requirement for a most perfect topographic match as attainable.

An ideal means and materials restoring tissue function and facilitating reconstruction of the morphology of such tissue is as yet, lacking.

SUMMARY OF THE INVENTION

In some embodiments, the present invention provides optimized processes/methods and tools/kits/means for implanting solid substrates for treatment of bone, cartilage, osteochondral or osteoarthritic disorders.

In some embodiments, the present invention provides optimized processes/methods and tools/kits/means for implanting solid substrates for promoting cell or tissue growth or restored function of osteochondral tissue.

In some embodiments, the present invention provides processes/methods and tools/kits/means for ensuring optimal cartilage regeneration in a subject with an osteochondral, bone or cartilage disease or disorder, which subject is being treated, inter alia, with the provision of an implant in an affected tissue site.

In some embodiments, the invention provides a process/method for optimal implantation of a solid substrate for promoting cell or tissue growth or restored function in an osteochondral, bone or cartilage tissue in a subject in need thereof.

In some embodiments, such process/method for optimal implantation of a solid substrate in an osteochondral, osteoarthritic joint, bone or cartilage tissue in a subject in need thereof comprises the step of selecting and/or preparing a solid substrate for implantation, which solid substrate has a length and width or that promotes a tight fit within the boundaries of the implantation site and is further characterized by a height sufficient such that when a first terminus of said solid substrate is implanted within a bone in a site for implantation, a second terminus of said solid substrate is at a height at least 2 mm less than an articular cartilage layer surface or is proximal to a tide mark region in said implantation site.

In some embodiments, the process/method comprises the step of implanting a solid substrate within a site for implantation to span a long axis of said site for implantation, wherein a first terminus of said implant is implanted within a bone at the basal surface of the implantation site and a second terminus is oriented apically such that said second terminus is at a height at least 2 mm less than the outer surface layer of articular cartilage into which such substrate has been implanted or at or substantially proximal to tide mark region, which separates the cartilage layer from the bone layer in said implantation site.

According to this aspect, and in some embodiments, such region above the implantation of the second terminus at a height at least 2 mm less than the outer surface layer of articular cartilage into which such substrate has been implanted results in a void between the boundary of the terminus and the surface layer of articular cartilage. In some embodiments, the method further comprises applying a biocompatible polymer layer to an apical surface of said implant, which layer fills the void area up to the level of the articular surface.

This invention provides the unexpected superior healing when application of optimally selected solid substrates useful in cell and tissue growth and/or restored function are specifically implanted within a site of tissue repair, whereby the solid substrate is substantially in a press fit/fight fit with respect to the length and width of the implantation site, yet the height of the solid substrate is approximately 2 mm below the articular cartilage layer in cartilage tissue proximal to the site of implantation. FIG. 3 specifically demonstrates improved healing and articular cartilage regeneration at the apical region above the implantation site, as a consequence of the methods of implantation as described and exemplified herein.

In particular, this invention provides the unexpected application that bone regeneration, repair and enhancement of formation is optimal when the solid substrate is characterized by being implanted within a site of tissue repair, whereby the solid substrate is substantially in a press fit/fight fit with respect to the length and width of the implantation site, yet the height of the solid substrate is approximately 2 mm below the articular cartilage layer in cartilage tissue proximal to the site of implantation.

In other embodiments, this invention provides the unexpected advantage in terms of greater chondrogenesis, when the solid substrate is characterized by being implanted within a site of tissue repair, whereby the solid substrate is substantially in a press fit/tight fit with respect to the length and width of the implantation site, yet the height of the solid substrate is approximately 2 mm below the articular cartilage layer in cartilage tissue proximal to the site of implantation.

In some embodiments, this invention provides a method for optimal implantation of a solid substrate for promoting cell or tissue growth or restored function for the treatment of osteoarthritis, bone disorders, osteochondral defects, or cartilage lesions in a subject in need thereof, said method comprising:

selecting and preparing a solid substrate for the treatment of or promoting cell or tissue growth or restored function for stable implantation in a region traversing bone and cartilage in a subject, which solid substrate has a length and width or that promotes a tight fit within the boundaries of the implantation site and is further characterized by a height sufficient such that when a first terminus of said solid substrate is implanted within bone in a site for implantation, a second terminus of said solid substrate is at a height at least 2 mm less than an articular cartilage layer surface or proximal to a tide mark region in said implantation site;

implanting said selected and prepared solid substrate within a site for implantation to span a basal to apical long axis of said site for implantation, wherein a first terminus of said implant is implanted within bone at the basal surface and a second terminus is oriented apically such that said second terminus is at a height at least 2 mm less than an articular cartilage layer surface or is proximal to a tide mark region in said implantation site such that a void is formed between an apical surface of said substrate and an articular cartilage layer; and optionally applying a biocompatible polymer layer or hydrogel or therapeutic compound or cell population or combination thereof, to an apical surface of said implant to fill said void formed between said second terminus and said articular cartilage layer.

In some embodiments, the invention provides for the use of a solid substrate for promoting cell or tissue growth or restored function in the manufacture of a product for the treatment of osteoarthritis, bone disorders, osteochondral defects, or cartilage lesions in a subject in need thereof, wherein said solid substrate for the treatment of or promoting cell or tissue growth or restored function is for stable implantation in a region traversing bone and cartilage in a subject, which solid substrate has a length and width or that promotes a tight fit within the boundaries of the implantation site and is further characterized by a height sufficient such that when a first terminus of said solid substrate is implanted within bone at the basal surface, a second terminus of said solid substrate is oriented apically and is at a height at least 2 mm less than an articular cartilage layer surface or proximal to a tide mark region in said implantation site such that a void is formed between an apical surface of said substrate and an articular cartilage layer.

In some embodiments, the substrate has a height of between 1-18 mm, and in some embodiments, the solid substrate has a height of between 5 and 10 mm. In some embodiments, the solid substrate has a diameter of about 1-35 mm.

In some embodiments, the methods/uses of this invention include implantation of more than one solid substrate in a tissue site as described, and in some aspects, care is taken such that the two implanted substrates are implanted such that the first terminus is implanted within bone and the second terminus of each substrate is oriented to be at a height at least 2 mm less than the outer surface layer of articular cartilage into which such substrate has been implanted or substantially proximal to tide mark region in said implantation site, as described, where there is a distance of approximately 3-10 mm between the two, or more, substrates being implanted in the tissue site, so each substrate is fully confined by bone In some embodiments, the solid substrate comprises a coral or coral derivative. In some embodiments, the coral or coral derivative solid substrate is characterized by a specific fluid uptake capacity value of at least 75% or is characterized by having a contact angle value of less than 60 degrees, when in contact with a fluid or which solid substrate is an allograft, autograft or xenograft, and which solid substrate is further characterized by tapered sides.

In some embodiments, establishing a specific fluid uptake capacity value of said solid substrate comprises the step of contacting said solid substrate with a fluid for from 0.1-15 minutes, allowing for spontaneous fluid uptake of said fluid within said solid substrate to arrive at said spontaneous fluid uptake value. In some embodiments, establishing a specific fluid uptake capacity value of said solid substrate further comprises the step of contacting said solid substrate with a fluid and applying negative pressure to said solid substrate to promote maximal uptake of said fluid within said solid substrate to arrive at a total fluid uptake value. In some embodiments, said fluid is a protein-containing, salt-containing or carbohydrate containing solution. In some embodiments, said fluid is a biologic fluid or a blood analog or a synthetic blood analog. In some embodiments, said specific fluid uptake capacity value is a function of change in weight in said marine organism skeletal derivative-based solid material.

In some embodiments, said specific fluid uptake capacity value is a function of change in fluid volume of applied fluid to said marine organism skeletal derivative-based solid material. In some embodiments, said biologic fluid is autologous with respect to a cell or tissue of a subject when said solid substrate is contacted with a cell or tissue of said subject. In some embodiments, said fluid is water.

In some embodiments, the solid substrate has a height of between 1-20 mm and in some embodiments, the said solid substrate has a diameter of about 1-50 mm. In some embodiments, the solid substrate is further characterized by tapered sides and in some embodiments, the solid substrate is further characterized by comprising tapered sides at an angle of from 0.75 to about 4 degrees from a longitudinal axis along said solid substrate. In some embodiments, the tapered sides are at an angle of about two degrees from a longitudinal axis along said solid substrate.

In some embodiments, the solid substrate is characterized by a conical or pyramidal frustum shape and optionally assumes a general shape of a bar, a plate, a cube a cylinder a cone or a screw. In some embodiments, the solid substrate comprises a coral or coral derivative, including essentially aragonite, calcite, hydroxyapatite or a combination thereof.

In some embodiments, the solid substrate for use in accordance with the methods as described herein is further characterized by at least one substantially flat cross section at a terminus of said solid substrate and tapered sides. In some embodiments, the solid substrate for use in accordance with the methods as described herein is further characterized as having sides at an angle of from 0.75 to about 4 degrees from a longitudinal axis along said solid substrate and in some embodiments, from about two degrees from a longitudinal axis along said solid substrate. In some embodiments, the solid substrate for use in accordance with the methods as described herein is further characterized by a conical or pyramidal frustum shape.

In some embodiments, the solid substrate for use in accordance with the methods as described herein is an allograft, autograft or xenograft.

In some embodiments, the solid substrate for use in accordance with the methods as described herein is further characterized by containing a curved surface, which curved surface has a radius of curvature approximating a radius of curvature of a tissue to which the solid substrate is being applied or implanted within.

In some embodiments, the solid substrate for use in accordance with the methods as described herein is a coral or coral derivative, which in some embodiments is aragonite, calcite, mixtures thereof, or other polymorphs of the same. In some embodiments, the solid substrate is isolated from a *Porites* species, a *Goniopora*, a *Millepora* species or an *Acropora* species.

In some embodiments, the solid substrate is isolated from enriched coral.

In some embodiments, the term "enriched" with respect to solid implants as herein described, in particular, with respect to coral, may refer to materials coated or impregnated with bone and cartilage growth promoting agents or materials. Such enrichment may be introduced by applying the materials directly to the implant, e.g. surface treatment of coral implants, or in some embodiments, such enrichment may be introduced by enriching the growth media in which the coral grows, either in natural or artificial habitats.

For example, U.S. Pat. No. 7,008,450 discloses a method of affecting a coral surface by coating coral with silicium, magnesium and phosphate by a hydrothermic procedure to obtain a surface of hydroxyapatite with 0.6 wt % of silicium, which would be considered to be an embodied "enriched coral" as herein described. In some aspects, "enriched coral" includes mineral structure and/or chemical modification of the coral (e.g., farmed raised, captive-bred corals), in its habitat (e.g. natural habitat, artificial habitat), during its growth and mineralization, for example, as described in U.S. Pat. No. 7,704,561, or Y. Uema et al., "Silicon-rich Coral Sand Improves Bone Metabolism and Bone Mechanical Properties in Mice," 59 J. Japanese Soc'y of Nutritional Food Science 265-70 1138-49 (2006), which are expressly incorporated by reference in their entirety. In some aspects, coral treatment as described in PCT International Application Publication Number WO/2012/038962 is contemplated for use in accordance with the methods and materials of this invention and is encompassed by the term "enriched coral", as used herein.

It will be appreciated that use of any coral, whether in natural habitat or artificial habitat, further enriched for certain desired properties/components, is contemplated herein and is encompassed by the term "enriched coral".

In some embodiments, the solid substrate comprises a hollow or hollows along a Cartesian coordinate axis of said solid substrate. In some embodiments, the hollow or hollows are along an axis substantially spanning from said second terminus toward said first terminus. In some embodiments, the hollow or hollows are along an axis extending from said second terminus up to half the height of said solid substrate, toward said first terminus. In some embodiments, the hollow or hollows are along an axis extending from said second terminus up to 30% of the height of said solid substrate, toward said first terminus. In some embodiments, the biocompatible polymer is absorbed within regions proximal to or within said hollow or hollows. In some embodiments, the solid substrate is an allograft or autograft or xenograft or allograft derivative or autograft derivative or xenograft derivative. In some embodiments, the biocompatible polymer comprises a natural polymer comprising a glycosaminoglycan, collagen, fibrin, elastin, silk, chitosan, alginate, calcium alginate, cross linked calcium alginate, cross linked chitosan, hyaluronic acid, sodium hyaluronate, cross linked hyalronic and any combinations thereof.

In some embodiments, the solid substrate further comprises a cytokine, a growth factor, a therapeutic compound, a drug, cell population or any combination thereof.

In some embodiments, the solid substrate has an overall shape that is ovoid or ellipsoid. In some embodiments, the solid substrate comprises an oval contour.

In some embodiments, the implanting is conducted at an implant angle of from about 0.75 to about 4 degrees from an axis perpendicular to the surface of the tissue site being thus treated. In some embodiments, the implanting is conducted at an implant angle of from about 2 degrees from an axis perpendicular to the surface of the tissue site being thus treated. In some embodiments, the solid substrate further comprises a bone filler or bone substitute material or osteoconductive material. In some embodiments, the method further comprises the step of contacting said solid substrate with cells or tissue pre-operative, intra-operative or post-operative. In some embodiments, the cells are composed of stem cell, chondrocyte osteoblast, bone marrow cell, stromal cell, embryonic cell, precursor cell, progenitor cell or a combination thereof. In some embodiments, contacting promotes adhesion, proliferation or differentiation, or a combination thereof, of said cells or cells within said tissue.

In some embodiments, the solid substrate promotes cell or tissue growth or restored function in tissue a subject afflicted with a defect or disorder or disease of the cartilage or bone or a combination thereof. In some embodiments, the cartilage defect or disorder or disease comprises a full or partial thickness articular cartilage defect; osteochondral defect; osteoarthritis, avascular necrosis; osteochondritis dissecans; bone cyst, non-union fractures, fracture, bone defect, bone edema, osteoporosis a joint defect or a defect resulting from trauma, sports, or repetitive stress. In some embodiments, the method serves to delay or eliminate the need for full or partial joint replacement in an affected subject. In some embodiments, the method serves to resurface an affected joint in a subject. In some embodiments, the method may be accomplished via automated systems for both preparation and implantation of said solid substrate. In some embodiments, the automated system may make use of robotic systems. In some embodiments, the method may provide an optimal customized implant and implantation.

In some embodiments, this invention provides for the use of a solid substrate for promoting cell or tissue growth or restored function in the treatment of osteoarthritis, bone disorders, osteochondral defects, or cartilage lesions in a subject in need thereof wherein said solid substrate for the treatment of or promoting cell or tissue growth or restored function is for stable implantation in a region traversing bone and cartilage in a subject, which solid substrate has a length and width or that promotes a tight fit within the boundaries of the implantation site and is further characterized by a height sufficient such that when a first terminus of said solid substrate is implanted within bone at the basal surface, a second terminus of said solid substrate is oriented apically and is at a height at least 2 mm less than an articular cartilage layer surface or proximal to a tide mark region in said implantation site such that a void is formed between an apical surface of said substrate and an articular cartilage layer.

It will be appreciated that the various embodied aspects of the methods described hereinabove are equally applicable to the described uses herein.

This invention provides in some embodiments a cartilage cutter, comprising:
  an elongated handle;
  a head region connected to said elongated handle, said head region further comprising
    an apical portion which connects with said elongated handle;
    a basal portion which inserts within an implantation site;
    a first and second angled side regions, which taper from said apical portion toward said basal portion;
  Wherein said first angled side region further comprises:
    a tapered blade surface,
    a supporting tapered angled surface opposingly positioned to said tapered blade surface; and
    a hollowed region located therebetween,
  whereby tissue in contact with said tapered blade surface cut thereby is of a thickness accommodating insertion within said hollowed region.

As is described herein, for example, with regard to FIGS. 1A-1S, unexpected superior healing and/or bone regeneration and/or greater chondrogenesis was found with the application of optimally selected solid substrates specifically implanted within a site of tissue repair in a press fit/fight fit with respect to the length and width of the implantation site, yet the height of the solid substrate is approximately 2 mm below the articular cartilage layer in cartilage tissue proximal to the site of implantation. FIG. 3 specifically demonstrates improved healing and articular cartilage regeneration at the apical region above the implantation site, as a consequence of the methods of implantation as described and exemplified herein. In some aspects, the tools and protocols to accomplish same are exemplified with respect to the description of FIGS. 1A-1S, and in some aspects, the cartilage cutter as herein described is uniquely adapted to perfect the methods/uses of this invention promoting ideal cartilage trimming to achieve the ability to position the solid substrate in a press fit/tight fit manner, and 2 mm below the articular cartilage layer in cartilage tissue proximal to the site of implantation.

In some aspects, and representing embodiments of this invention, the cartilage cutter head region connects to the elongated handle portion for ease of gripping, which in some aspects is ergonomic. In some aspects, the cartilage cutter head region basal portion inserts within an implantation site; and is angled by means of the first and second angled side regions of the head region, which angled side regions taper from the apical portion toward said basal portion; and such tapering promotes a proper fit within the implantation site being produced for insert of a tapered solid substrate therewithin.

It will be understood that the term "tapered" with respect to elements of the cartilage cutter refers to the incremental angling or taper with respect to a longitudinal axis through such implantation site.

The first angled side region of the cartilage cutter head region will further comprise a tapered blade surface and a supporting tapered angled surface opposingly positioned to the tapered blade surface; and a hollowed region located therebetween. As will be appreciated by the skilled artisan, such arrangement of the tapered blades surface, supporting tapered angled surface opposingly positioned to the tapered blade surface; and hollowed region located therebetween facilitates insertion of the tissue in contact with the tapered blade surface and cut thereby therewithin and further regulates the thickness of the tissue being cut thereby for insertion within said hollowed region.

In some embodiments, the interior region between said first and second angled side regions is substantially hollowed, or in some embodiments, the interior region between said first and second angled side regions is substantially solid but contains a hollowed region into which the cut tissue may insert.

In some embodiments, the basal surface of the cartilage cutter head region is substantially flat or in some embodiments, is ensured to smoothly insert within the implantation site so that insertion of the cartilage cutter within the implantation site does not in any way negatively impact insertion of the solid substrate within the implantation site.

In some embodiments, the cartilage cutter handle contains an elongated portion to be comfortably gripped by the user and in some embodiments, the handle has a grip surface and in some embodiments, the elongated handle is constructed to be ergonomic. In some embodiments, the elongated handle may be removably attached to said head region. For example and referring to FIG. 5F, the handle may be removable by adaptation of the connector region of the handle and head region.

The skilled artisan will appreciate that various permutations/solutions may be devised to removably connect the head region and handle, and the connection point may be at any appropriate location, such as, for example, immediately proximal to the head region, or at a reasonable distance from the base of the head region, etc.

In some embodiments the head region is scalable to accommodate a range in dimensions of a tissue site where cartilage cutting is desired.

In some embodiments, this invention provides a kit of parts comprising the cartilage cutter as herein described. For example, and in some embodiments, the tools depicted in FIGS. 1A-1S may all be provided in a single kit or select tools from the complement of tools depicted in FIGS. 1A-1S may be provided as part of a kit, and same is envisioned as an embodied aspect of the subject application.

In some embodiments, this invention provides a method for optimal implantation of a solid substrate for promoting cell or tissue growth or restored function for the treatment of osteoarthritis, bone disorders, osteochondral defects, or cartilage lesions in a subject in need thereof, said method comprising:
  selecting and preparing a solid substrate for the treatment of or promoting cell or tissue growth or restored function for stable implantation in a region traversing bone and cartilage in a subject, which solid substrate has a length and width or that promotes a tight fit within the boundaries of the implantation site and is further characterized by a height sufficient such that when a first terminus of said solid substrate is implanted within bone in a site for implantation, a second terminus of said solid substrate is at a height at least 2 mm less than an articular cartilage layer surface or proximal to a tide mark region in said implantation site;
  implanting said selected and prepared solid substrate within a site for implantation to span a basal to apical long axis of said site for implantation, wherein a first terminus of said implant is implanted within bone at the basal surface and a second terminus is oriented apically such that said second terminus is at a height at least 2 mm less than an articular cartilage layer surface or is proximal to a tide mark region in said implantation site such that a void is formed between an apical surface of said substrate and an articular cartilage layer; wherein said site of implantation has been prepared for insertion of said solid substrate by creating a void of desired dimensions in terms of depth, length and width, and the side walls of the site for implantation have been created to contain a taper, and cartilage tissue within said site for implantation has been removed with the aid of the cartilage cutter as herein described, and optionally
  applying a biocompatible polymer layer or hydrogel or therapeutic compound or cell population or combination thereof, to an apical surface of said implant to fill said void formed between said second terminus and said articular cartilage layer surface.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

FIGS. 1A-1T schematically depict a generalized procedure for preparing a defect site for implantation. FIGS. 1A-1E depict applying an implantation alignment tool 1-10 and inserting therethrough a rod-like structure 1-20, therethrough, at an angle essentially 90 degrees/perpendicular to the tissue surface, whereby the rod-like structure is the drilled into the underlying subchondral bone 1-30 (FIG. 1D) and the alignment tool may contain markings 1-50 (FIG. 1E) serving as indicator for the depth at which the rod-like structure may be drilled/advanced therein and subsequent removal of the alignment tool. FIGS. 1F-1I depict drilling/expanding the site for implant insertion. A drill sleeve 1-60 is placed over the rod-like structure 1-20, with the sleeve potentially/optionally containing a terminus adapted to insert stably in the underlying tissue and a specialized drill, may be adapted to promote/facilitate rotation of a drill bit 1-70 while placed over the rod-like structure (FIG. 1H), but within the drill sleeve 1-60. The drill bit and drill sleeve are then removed (FIG. 1I), while the rod-like structure is maintained in place, embedded in the subchondral bone.

FIGS. 1J through 1M depict use of a tissue reamer 1-80, which may be rotated as depicted in FIG. 1K, with the terminal modifications of the reamer expanding/enlarging the walls of the implantation site within the cartilage and subchondral bone and subsequent removal (FIG. 1M) of the reamer followed by tissue site washing, as depicted in FIG. 1N. FIGS. 1O-1R depict use of a tissue shaper. The tissue walls of the implant may be further processed, using a tissue shaper 1-110, and following completion of the tissue shaping, the shaper, as well may be removed from the site, as depicted in FIG. 1R, followed by washing of the tissue site, as depicted in FIG. 1S and the tissue site may be shaped/ smoothed/expanded or further shaped/smoothed/expanded with the aid of a cartilage cutter 1-120 (depicted in FIG. 1T) as described further herein or scalpel or other appropriate tool.

FIGS. 2A-2D schematically depict first introduction of an implant in a site in need of osteochondral repair, or bone repair or cartilage repair. The implant 2-130 is inserted in the prepared tissue site manually, as depicted in FIG. 2B, pressed to fit therein as depicted in FIG. 2C so that the implant is initially introduced/placed within the site of repair as depicted in FIG. 2D. A tamper 2-140 as depicted in FIGS. 2E and 2F is then used to further advance the implant in the site of desired repair, to further advance the implant in a press fit manner, such as that depicted in FIG. 2H facilitates implant insertion to the bone in the defect site, where the upper boundary of the implant is no longer flush with the articular cartilage layer, but instead is approximately 2 mm below the articular cartilage surface. FIGS. 2J-2K depict the application of a biocompatible/therapeutic polymer composition to the apex of the implant 2-160 with a syringe 2-170. FIG. 2I depicts implantation of more than one solid substrate 2-130, as described. FIG. 2L shows a transverse section through the region in FIG. 2G of implantation of the substrate at within bone and that the implant spans apically to a region about 2 mm lower than the articular cartilage surface layer.

Figures 3A, 3B, 3C:
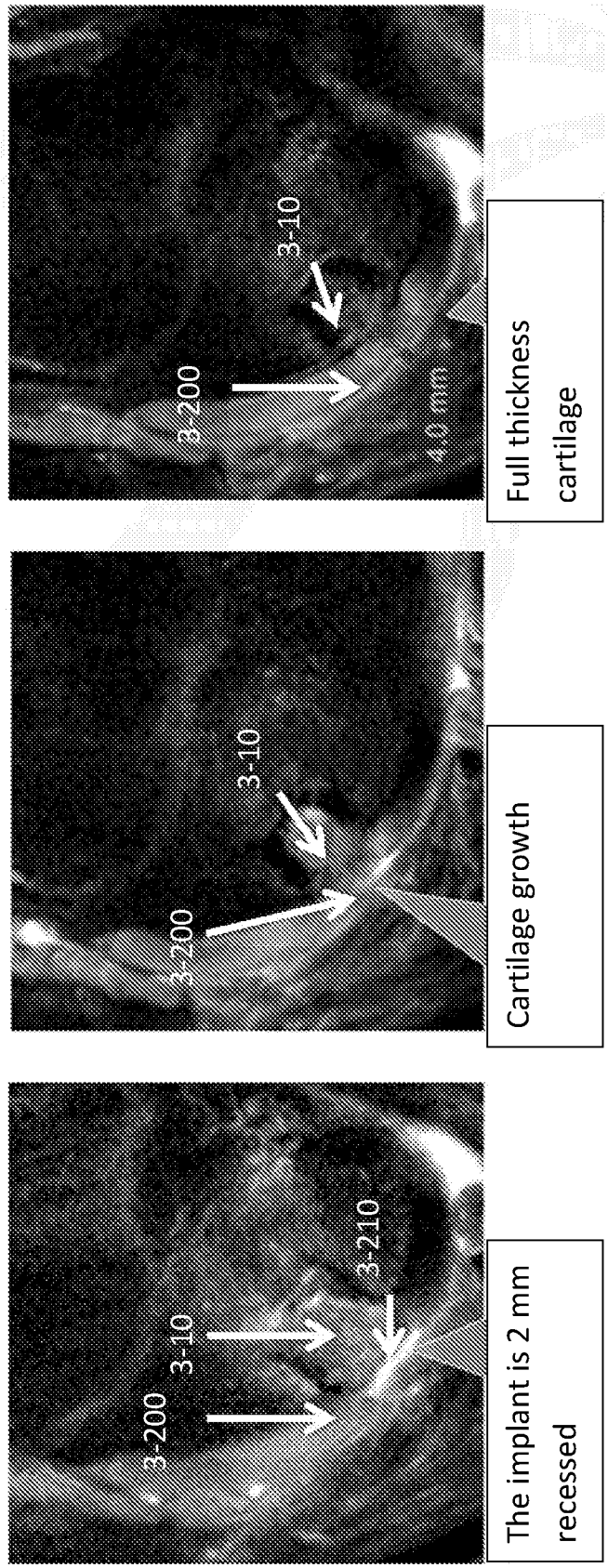

FIG. 3A-3C describe MRI results of human patients participating in a clinical trial showing full thickness regeneration of the articular cartilage surface in the subjects following their treatment by the embodied methods of this invention.

FIG. 4A-4H describe comparative results of two patients in whom a solid substrate was implanted, and demonstrating unexpectedly superior results in a patient treated according to an embodied method of this invention. FIGS. 4A-4D, as compared to FIGS. 4E-4H, demonstrate healing of a defect site, but without reformation of a tidemark and full cartilage thickness in the region most proximal to the implantation site.

FIG. 5A-5I describes the cartilage cutter and highlights certain key features of same.

DETAILED DESCRIPTION OF THE PRESENT INVENTION

This invention provides, inter alia, optimized methods for implantation of solid substrates for promoting cell or tissue growth or restored function.

In some embodiments, the present invention provides optimized methods and means for implanting solid substrates for promoting cell or tissue growth or restored function of osteochondral tissue.

In some embodiments, the present invention provides means and methods for ensuring optimal cartilage regeneration in a subject with osteoarthritis, or an osteochondral, bone or cartilage disease or disorder, which subject is being treated, inter alia, with the provision of an implant in an affected tissue site.

In some embodiments, the invention provides a method for optimal implantation of a solid substrate for promoting cell or tissue growth or restored function in an osteoarthritic, osteochondral, bone or cartilage tissue in a subject in need thereof.

In some aspects the methods of this invention promote treating osteoarthritis, or a bone, cartilage or osteochondral disease or disorder.

The terms "treating" and "treatment" when used in connection with a disease or condition refer to executing a protocol that may include a cartilage, bone and/or osteochondral repair procedure, in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. In some embodiments, the bone, cartilage and/or osteochondral repair implant can be used to treat subchondral, osteochondral, or cartilage defects.

The term "subchondral" includes an area underlying the articular cartilage. The term "subchondral bone" includes a layer of bone just below a zone of cartilage. "Osteochondral" includes a combined area of cartilage and bone where a lesion or lesions can occur. "Osteochondral defect" includes a lesion which is a composite lesion of cartilage and subchondral bone. "cartilage" includes cartilage containing groups of isogenous chondrocytes located within lacunae cavities which are scattered throughout an extracellular collagen matrix.

Methods/uses/tools/kits are provided that improve bone, cartilage and/or osteochondral repair. Through the methods as described herein for implantation of the described substrate, the growth of bone, cartilage and/or related tissue may be facilitated particularly when repairing bone, cartilage and/or osteochondral defects.

In some embodiments, methods of implantation of solid substrates for the treatment of bone, cartilage and/or osteochondral repair are provided, comprising a tissue scaffold configured to allow growth of at least bone and/or cartilage.

The tissue scaffolds provides a matrix for the cells to guide the process of tissue formation in vivo in three dimensions. The morphology of the scaffold guides cell migration and cells are able to migrate into or over the scaffold, respectively, and the creation of a discrete void in the cartilage layer above the solid substrate, for example for application of the hydrogel or therapeutic solution incorporation reduces inflammation/irritation at the implantation site and/or otherwise promotes incorporation of the implant, regeneration of cartilage and/or bone tissue and/or healing at the site.

In some embodiments, such method for optimal implantation of a solid substrate for promoting cell or tissue growth or restored function in an osteochondral, bone or cartilage tissue in a subject in need thereof comprises the step of selecting and/or preparing a solid substrate for promoting cell or tissue growth or restored function for implantation, which solid substrate has a length and width or that promotes a tight fit within the boundaries of the length and width of the implantation site and is further characterized by a height sufficient such that when a first terminus of said solid substrate is implanted within bone in the implantation site, a second terminus of said solid substrate is at a height at least 2 mm less than an articular cartilage layer surface or is proximal to a tide mark region in said implantation site.

In some embodiments, the method comprises the step of implanting a solid substrate within a site for implantation to span a long axis of said site for implantation, wherein a first terminus of said implant is implanted within bone and a second terminus is oriented apically such that said second terminus is at a height at least 2 mm less than an articular cartilage layer surface or is proximal to a tide mark region in said implantation site.

It will be understood that reference to the term "tide mark" is meant to convey the plain and conventional meanings of same. For example, and in some embodiments, the term "tide mark" encompasses the layer of calcified cartilage separating hyaline cartilage from bone in a joint. In some aspects, the term "tide mark" is meant to refer to the calcified cartilage layer attaching hyaline cartilage to bone. In some aspects, reference to the term "tide mark" is with regard to the boundary line between the calcified cartilage and hyaline cartilage. In some aspects, the term "tide mark" refers broadly to the entire region of tissue bridging the cartilage to bone tissues in a joint.

It will be further appreciated that the methods/uses and means of this invention contemplate implantation of the solid substrate as described, where an apical surface of the substrate reaches to the lower ⅓ of the cartilage layer into which the substrate is being implanted.

For example, and in some embodiments, if the cartilage layer is thicker, then implantation may be such that the apical region of the substrate is more than 2 mm from the articular cartilage surface. In some embodiments, implantation occurs at or near the tidemark, and in some embodiments, the implant is within the lower third of the cartilage layer and the upper two thirds of the cartilage layer are open to the environment and same may be a height of more than 2 mm. For example, and in some embodiments, if the cartilage layer is thinner, then implantation may be such that the apical region of the substrate is less than 2 mm from the articular cartilage surface. In some embodiments, implantation occurs at or near the tidemark, and in some embodiments, the implant is within the lower third of the cartilage layer and the upper two thirds of the cartilage layer are open to the environment and same may be a height of less than 2 mm.

It will be appreciated that the invention contemplates methods/uses and means where the solid substrate is implanted within bone spanning upward toward the cartilage layer, whereby the apex of the implant is: 1) at least 2 mm below the articular cartilage layer; or 2) at or proximal to the tidemark; or 3) within the lower ⅓ of the full cartilage tissue proximal to the site of implantation and all of the above are to be considered envisioned embodiments of the invention.

In some embodiments, as noted the methods/uses and means include a first terminus of the solid substrate being implanted within bone tissue, in the implantation site.

According to this aspect, and in some embodiments, implantation in bone promotes access to underlying cells involved in bone and/or cartilage healing and/or regeneration. In other embodiments, implantation in bone provides a scaffold whereby cells and/or factors involved in bone and/or cartilage healing and/or regeneration access the implantation site and/or solid substrate and promote cartilage and/or bone healing and/or regeneration.

In some embodiments, the implantation within bone is such that care is taken to avoid implantation in the bone growth plate in the subject.

In some embodiments, implantation within bone is such that the solid substrate penetrates into underlying bone tissue at a depth and/or level such that promotes stable scaffold incorporation and consideration with respect to the nature of the solid substrate and its mechanical stability needs and/or the nature of the bone into which the solid substrate is being implanted and/or the age and frailty of the bone tissue are all considered and taken into account, as will be appreciated by the skilled artisan.

Any appropriate substrate that promotes cartilage, bone or osteochondral repair or regeneration is envisioned for use in accordance with the methods of this invention.

In some aspects, the implant is an implant, such as that described, for example as described in United States Patent Application Publication Numbers 2007029951, 20040192605, 20100049322, 20070276506 and U.S. Pat. Nos. 8,518,433, 9,168,140 and 7,931,687, and others, each of which is fully incorporated herein by reference.

In some aspects, the implant is an implant, such as that described, for example as described in European Patent Number EP1447104B1, PCT International Application Publication Numbers WO2012063201A1, WO2011064724A1, and U.S. Patent Application Publication Numbers US20140134258A1, US20130129634A1, WO/2012/038962 and the like.

In some embodiments, the implant is any implant recognized in the state of the art. For example, and representing envisioned embodiments of the invention, a number of commercially available implants and well described implants may used in accordance with this invention and representing embodiments of this invention, including, inter alia, U.S. Pat. No. 9,211,126, US20100191245, US20100268239, U.S. Pat. Nos. 7,029,479, 8,864,827, US20170311983, US20120271417, US20120191187, US20150250602, US20170360566, US20160022280, US20160022279, US20160106444, U.S. Pat. No. 7,896,885, US20170303934, U.S. Pat. No. 8,540,717, US20150250475, US20110152870, US20170119528, US20100312342, U.S. Pat. No. 9,204,873, US20140012267, US20150250594, U.S. Pat. No. 9,510,840, US20140309689, U.S. Pat. Nos. 9,572,587, 8,177,841, US20140012389, US20080033443, U.S. Pat. Nos. 7,713,305, 9,358,029, 7,896,883, US20080172125, U.S. Pat. No. 9,055,955, US20080183174, U.S. Pat. No. 9,668,757, US20110152869, US20140288561, U.S. Pat. Nos. 8,556,902, 7,914,545, US20170100251, US20170128085, US20090192516, US20090216285, U.S. Pat. Nos. 9,283,076, 6,610,067, 7,901,408, US20080195113, US20120253365, U.S. Pat. No. 9,468,448, each of which is incorporated by reference, fully herein and others.

In some embodiments, the implants, which may used in accordance with this invention and representing embodiments of this invention, include, inter alia, U.S. Pat. Nos. 8,012,206, 8,162,947, 5,895,425, US20140350688, U.S. Pat. No. 9,603,712, WO/2013/153435A1, U.S. Pat. No. 9,510,951, US20140379089, US20150134066, US20160166301, U.S. Pat. No. 7,264,634, US20170367827, WO/2004/014303A2, U.S. Pat. No. 8,211,112, WO/2016/099620A1, US20150142052, U.S. Pat. No. 8,961,538, US20130150885, U.S. Pat. Nos. 9,216,090, 8,430,909, US20130245775, U.S. Pat. No. 7,820,638, WO/2014/202494A1, WO/2004/014303, U.S. Pat. Nos. 7,959,636, 8,591,592, 7,160,305, US20010053934, US20130338792, US20170304076, US20150010606, U.S. Pat. Nos. 7,862,567, 6,623,524, US20170367741, U.S. Pat. No. 9,610,167, U.S. Pat. Nos. 9,216,091, 8,512,410, US20130238099, U.S. Pat. No. 8,663,279, US20170360569, U.S. Pat. Nos. 8,512,411, 8,876,900, 8,409,209, 8,888,785, 7,967,823, 7,993,369, US20090187216, U.S. Pat. Nos. 8,540,777, 8,167,951 and US20160095709, each of which is incorporated by reference, fully herein and others.

In some embodiments, the implants, which may used in accordance with this invention and representing embodiments of this invention, include, inter alia, US20070202084, US20020071855, WO/2002/009792, U.S. Pat. Nos. 5,443,473, 6,548,081, US20020128512, US20170326271, US20170312385, U.S. Pat. No. 8,865,964, US20110312912, US20160082038, US20110196328, US20050222083, US20040038934, WO/2002/068383, US20130045945, U.S. Pat. No. 6,620,927, WO/2013/156547, U.S. Pat. No. 8,124,120, US20070203095, U.S. Pat. No. 5,621,093, US20050136122, U.S. Pat. Nos. 8,323,617, 6,884,788, 8,901,202, WO/2007/070546, WO/2007/070546, WO/2007/070617, U.S. Pat. Nos. 5,356,883, 6,096,727, 5,502,081, 6,537,979, 6,013,679, WO/2005/067994, WO/2017/189723, WO/2017/189733, WO/2007/070547, WO/2007/070547, U.S. Pat. No. 7,722,616, US20040044416, US20070196342, U.S. Pat. Nos. 7,842,487, 6,482,231, US20080317808, US20110104284, WO/1994/002517, US20100136081, U.S. Pat. No. 7,968,111, US20080097605 and US20070110819, each of which is incorporated by reference, fully herein and others.

In some embodiments, the implants, which may used in accordance with this invention and representing embodiments of this invention, including, inter alia, US20160287407, U.S. Pat. No. 9,155,543, WO/2016/161026, US20130006368, US20160287392, U.S. Pat. No. 9,526,632, WO/2016/161025, US20160038308, U.S. Pat. No. 9,737,294, US20150351815, US20140214080, WO/2014/117107, US20170165074, US20160302930, WO/2016/168363, WO/2012/162552, US20130211451 and US20050278025, each of which is incorporated by reference, fully herein and others.

In some embodiments, the implants, which may used in accordance with this invention and representing embodiments of this invention, including, inter alia, U.S. Pat. No. 8,071,083, WO/2003/020117, U.S. Pat. Nos. 7,942,934, 7,132,110, 8,460,685, 7,205,337, 6,309,659, 7,241,813, 6,623,748, 7,811,608, 6,180,606, 6,180,605, US20060251729, US20020034531, US20040022858, U.S. Pat. No. 6,311,690, WO/2004/060430, WO/2003/055933, U.S. Pat. No. 8,497,236, US20060136068, U.S. Pat. No. 8,945,535, US20110307010, WO/2011/009635, US20080306610, US20100003304, U.S. Pat. No. 4,472,840, US20090054906, US20110293584, US20050037978, U.S. Pat. Nos. 4,394,370, 7,147,846, US20020082697, US20040081704, US20120263683, US20080269895, U.S. Pat. Nos. 8,173,162, 6,679,918, 4,772,284, U.S. RE43714, WO/2007/094672, WO/2006/115398, US20010014667, WO/2008/154149, WO/2008/154149, US20080294270, US20120021008, U.S. Pat. No. 6,511,510, US20030044445, US20100034865 and US20110020419, each of which is incorporated by reference, fully herein and others.

In some embodiments, any commercially available implant product is envisioned for use in accordance with this invention.

In some aspects, the implant is an implant, such as that described, for example in U.S. Pat. Nos. 8,932,581, 8,808,725; 8,802,115; 8,790,681, or 9,770,531; or in United States Patent Applications Publication numbers 2015-0134065, 2015-0147397, 2015-0289889, 2016-0000969; or in PCT Application Publication Number WO/2016/178226, each of which is fully incorporated herein by reference.

In some embodiments, the invention provides an optimized solid substrate for promoting cell or tissue growth or restored function, which solid substrate comprises a coral or coral derivative, is characterized by a specific fluid uptake capacity value of at least 75% or is characterized by having a contact angle value of less than 60 degrees, when in contact with a fluid and which is optionally further characterized by tapered sides.

In some embodiments, the invention provides more generally for an optimized solid substrate for promoting cell or tissue growth or restored function, which solid substrate comprises a porous natural substrate, such as an allograft or autograft, or other suitable marine, plant or animal source material, which porous solid substrate is characterized by being absorptive of biologic fluids when implanted in situ, is of sufficient strength and hardness and useful in stimulating bone and/or cartilage repair and which substrate is optionally further characterized by tapered sides.

In some embodiments, the invention provides more generally for an optimized solid substrate for promoting cell or tissue growth or restored function, which solid substrate comprises a any substrate suitable for implantation such as metal, any suitable alloy, bioactive glasses and the like, PLGA, PGA, any appropriate carbon composite implant material, ceramic material, alginate-based implant, coral-based implant, including farmed or otherwise enriched coral-based implants, alcohols and others, as will be appreciated by the skilled artisan, which when implanted in situ, is of sufficient strength and hardness and useful in stimulating bone and/or cartilage repair, or bone and/or cartilage treatment, and which substrate is optionally further characterized by tapered sides.

In some embodiments, this invention provides an optimized solid substrate for promoting cell or tissue growth or restored function, which solid substrate is characterized by a specific fluid uptake capacity value of at least 75% or is characterized by having a contact angle value of less than 60 degrees, when in contact with a fluid and which is optionally further characterized by having at least a surface of said substrate having a radius of curvature that is substantially similar to a radius of curvature of a tissue surface to which such solid substrate is being applied/implanted within.

In some embodiments, this invention provides an optimized solid substrate for bone and/or cartilage treatment or restored function, which solid substrate is characterized by having at least a surface of said substrate having a radius of curvature that is substantially similar to a radius of curvature of a tissue surface.

According to these aspects and in some embodiments, any solid substrate as herein described may comprise a coral, or any other similar natural porous material which is plant or animal in source origin. In some aspects such substrate may comprise an allograft or autograft or xenograft. In some aspects, such substrate may comprise a plant material, such as bamboo.

In some aspects, the porous natural substrate may be acellular or further processed to be suitable for implantation within a human host.

In some aspects, a solid substrate as herein described may be characterized by comprising tapered sides. In some embodiments, the term "tapered sides" refers to the sides of the solid implant being at an angle of from 0.75 to about 4 degrees from a longitudinal axis along said solid substrate.

In some aspects, the solid substrate will be characterized by having at least one substantially flat cross section at a terminus of said solid substrate, and in some embodiments, the solid substrate will comprise a series of holes, channels or voids, in a region of the substrate that will be proximal to cartilage tissue to be treated by the methods of this invention. In some aspects, such solid substrate will be further characterized by a phase that is solid and optionally comprises pores, but no channels in a region of the substrate that is proximal to bone, when implanted in accordance with the methods of this invention.

In some aspects, the reference to being characterized by a substantially flat cross section of said solid substrate does not preclude the potential for rounded edges of the solid substrate, or in some embodiments, a slightly rounded top or bottom surface. In some embodiments, according to this aspect, the solid substrate may have slight bumps or other imperfections at either terminus. In some embodiments, according to this aspect, the solid substrate will be slightly rounded, but without a terminal point or pointed end or ends. In some embodiments, one terminus may be more rounded in appearance than another. In some embodiments, a terminus may be further characterized by the presence of a series of longitudinal channels or voids created therein, however, the top surface may still be considered to be substantially flat, as the surface in overall appearance will be substantially flat.

In some aspects, the solid substrate will have a substantially conical shape.

In some aspects, the term "a substantially conical" with regard to shape refers to a solid substrate characterized as above, with a shape approximating a cone in that it possesses a circular cross section at each terminus of the substrate, and tapered sides. In some aspects, the term "a substantially conical" precludes the presence of a terminal sharp point in the substrate, but does encompass a shape approximating a cone shape, whereby a pointy end is shaved or removed, leaving a circular cross section, tapered end in its stead.

According to this aspect, and in some embodiments, the solid substrate is characterized by a conical frustum shape.

According to this aspect, and in some embodiments, the solid substrate is characterized by a conical frustum shape, i.e. a portion of a solid cone that lies between two parallel planes cutting same. In some aspects, the diameter of the two parallel planes cutting the solid cone differs, such that one is larger and one is smaller. In some embodiments, the solid substrate characterized by a conical frustum shape will be further characterized by insertion of the solid substrate within an osteochondral defect such that the plane characterized with a smaller diameter is inserted first, such that the plane characterized by the larger diameter is most apically located within the implantation site.

In some aspects, the solid substrate will have a substantially pyramidal shape.

In some aspects, the term "a substantially pyramidal" with regard to shape refers to a solid substrate characterized as above, with a shape approximating a pyramid in that it possesses a flat cross section at each terminus of the substrate, and tapered sides. In some aspects, the term "substantially pyramidal" precludes the presence of a terminal sharp point in the substrate, but does encompass a shape approximating a pyramid shape, whereby a pointy end is shaved or removed, leaving a flat cross section, tapered end in its stead.

According to this aspect, and in some embodiments, the solid substrate is characterized by a pyramidal frustum shape.

According to this aspect, and in some embodiments, the solid substrate is characterized by a pyramidal frustum shape, i.e. a portion of a solid pyramid that lies between two parallel planes cutting same. In some aspects, the length/width of the two parallel planes cutting the solid pyramid differs, such that one is larger and one is smaller. In some embodiments, the solid substrate characterized by a pyramidal frustum shape will be further characterized by insertion of the solid substrate within an osteochondral defect such that the plane characterized with a smaller length/width is inserted first, such that the plane characterized by the larger length/width is most apically located within the implantation site.

In some embodiments, the solid substrate is characterized by a substantially ovoid shape, when referring to a shape regarding the boundaries or outer contour of the substrate.

In some aspects, the solid substrate is characterized by any shape, that permits tapered sides, and in some embodiments, substantially flat termini, which can accommodate an ideal, optimized press fit within a defect site. In some aspects, the solid substrate will assume any appropriate geometry approximating a bar, cube, oval, with tapered sides, i.e. a solid shape substantially resembling for example, a bar, a plate, cube or oval, with two parallel planes cutting same.

In some aspects, the solid substrate is characterized by a shape with tapered sides as described, that can approximate the overall shape of a talus, great toe, shoulder, condyle, ankle, patella, trochlea, pelvis, vertebra, hip and others, as will be appreciated by the skilled artisan, or approximate a smaller piece of same that can insert within such structures readily, and in an optimized press fit manner.

In some aspects, the solid substrate may be characterized by having a first end with a diameter varying in size of between about 50-97% from that of a second diameter of the second end of the substrate, or in some embodiments, the solid substrate may be characterized by having a first end with a diameter varying in size of between about 50-65% from that of a second diameter of the second end of the substrate, or having a first end with a diameter varying in size of between about 55-75% from that of a second diameter of the second end of the substrate, having a first end with a diameter varying in size of between about 70-85% from that of a second diameter of the second end of the substrate, having a first end with a diameter varying in size of between about 75-97% from that of a second diameter of the second end of the substrate, having a first end with a diameter varying in size of between about 60-95% from that of a second diameter of the second end of the substrate, having a first end with a diameter varying in size of between about 65-97% from that of a second diameter of the second end of the substrate, having a first end with a diameter varying in size of between about 80-98% from that of a second diameter of the second end of the substrate having a first end with a diameter varying in size of between about 70-85% from that of a second diameter of the second end of the substrate.

In some aspects, the tapered sides are at an angle of two degrees from a longitudinal axis along the solid substrate.

In some aspects, the tapered sides are at an angle of 0.5 to 6.5 degrees from a longitudinal axis along the solid substrate. In some aspects, the tapered sides are at an angle of 0.5 to 4 degrees from a longitudinal axis along the solid substrate. In some aspects, the tapered sides are at an angle of 0.75 to 3.5 degrees from a longitudinal axis along the solid substrate, or in some aspects, the tapered sides are at an angle of 1 to 3.25 degrees from a longitudinal axis along the solid substrate, or in some embodiments, the tapered sides are at an angle of 1.5 to 2.75 degrees from a longitudinal axis along the solid substrate, or in some embodiments, the tapered sides are at an angle of 1.75 to 4 degrees from a longitudinal axis along the solid substrate. Referring to FIG. 1B, an embodied solid substrate of the invention is shown, whereby the tapering of the lateral sides is evident, when viewed along a longitudinal axis drawn as depicted by the black bar spanning the implant.

The solid substrates of this invention may be characterized by a specific fluid uptake capacity value of at least 75%, which specific fluid uptake capacity value is determined by establishing a spontaneous fluid uptake value divided by a total fluid uptake value, or are characterized by having a contact angle value of less than 60 degrees, when in contact with a fluid. Methods for the determination of the specific fluid uptake and contact angle value have been described, for example, in PCT International Application Publication Number WO2014125478, hereby incorporated by reference in its entirety.

In some aspects, the solid substrate will be characterized by a curved cross section at a terminus of the solid substrate. According to this aspect, and in some embodiments, such curvature will be more typically at an apical surface of a solid substrate as herein described, in order to accommodate an appropriate fit of the implant, such that the correction of a defect containing a curved surface is readily accomplished. In some aspects, the curved surface of the defect site is substantially symmetrical and therefore the apical surface of the implant will comprise a substantially symmetrically curved surface. In some aspects, the curved surface of the defect site is substantially asymmetrical and therefore the apical surface of the implant will comprise a substantially asymmetrically curved surface.

In some embodiments, reference to a curved surface or curved cross section at a terminus of a solid substrate of this invention will include a radius of curvature of such substrate, where the radius may vary along an X-axis of a plane of a surface of such substrate, or in some embodiments, the radius may vary along a Z-axis of a plane of a surface of such substrate, or in some embodiments, radius may vary along an X-axis and a Z-axis of a plane of a surface of such substrate.

Similarly, and as described herein, reference to a curved surface or curved cross section at a terminus of a solid substrate of this invention will include a radius of curvature of such substrate, where the radius may vary along a coronal or sagittal plane of a surface of such substrate, or in some embodiments, such radius may vary along a lateral or anterior/posterior plane of a surface of such substrate, or in some embodiments, such radius may very along any axis as herein defined, along a surface of a substrate as herein described.

The solid substrates of this invention will, in some embodiments, comprise a coralline-based material. Coral, which is comprised of $CaCO_3$ in the crystalline form of aragonite or calcite has been shown to possess the advantage of supporting fast cellular invasion, adherence and proliferation. Coral has been shown to be an effective substrate for facilitation of the adherence, proliferation and differentiation of mesenchymal stem cells, and ultimate incorporation into cartilage and/or bone tissue. Coral has also been shown to serve as an excellent substrate for promoting adherence and proliferation of a number of other cell types, serving as an excellent support for cell and tissue growth.

The terms "coral" and "aragonite" and "calcite" may be used interchangeably herein.

In some embodiments, reference to an "implant" or "plug" or "solid substrate", as used herein refers to any embodiment or combined embodiments as herein described with regard to the solid substrates and to be considered as being included in the described aspect of this invention. For example, reference to a "solid substrate" as used herein, is to be understood to refer to any embodiment of a solid substrate as described herein being applicable for the indicated purpose or containing the indicated attribute, etc.

In one embodiment, "solid substrate" refers to a shaped platform used for cell and/or tissue repair and/or restored function, wherein the shaped platform provides a site for such repair and/or restored function. In one embodiment, the solid substrate is a temporary platform. In one embodiment, "temporary platform" refers to a natural degradation of a coral of this invention that occurs over time during such repair, wherein the natural fully or partially degradation of the coral may results in a change of solid substrate shape over time and/or change in solid substrate size over time.

In some embodiments, the solid implant is cannulated and in some embodiments, the solid implant is not cannulated.

It will be appreciated that different species of coral vary in terms of their average pore diameter and pore volume and the invention contemplates use of any such coral as a starting material for the preparation of the solid substrates as herein described, where the solid substrate is characterized in that it is characterized by a specific fluid uptake capacity value of at least 75%. As used herein, the term "pore volume" refers to volume or open spaces inside the porous scaffolding of this invention. Pore volume is determined by any means known in the art. Porosity can be calculated by standard methods, an example of which is provided further hereinbelow, see for example, Karageorgiou V, Kaplan D. (2005) "Porosity of 3D biomaterial scaffolds and osteogenesis" Biomaterials; 26(27):5474-91, which is hereby incorporated by reference in its entirety.

It will be appreciated that the term "coral" will refer to a starting material from which aragonite, calcium carbonate, calcite, or hydroxyapatite etc. may be isolated.

It will still further be appreciated that any substrate, as referred to herein, in particular, any coral substrate, is envisioned to encompass known existing forms of same, modifications of same, etc. For example, and representing specifically envisioned embodiments, if the solid substrate is coral-derived, then, in some aspects, such coral may be grown in an enriched medium or aquatic environment, and in some embodiments, such coral may be further processed including surface modifications, such as, for example, via cold plasma processing, as is known in the art and as described in the various patents and patent applications recited herein, all of which are fully incorporated by reference herein.

In some embodiments, Applicant specifically contemplates methods of preparation as described in PCT International Application Publication Number WO2014125478 and its description of cold plasma processing of coral-based implants, for inclusion in the methods of this invention.

It will be appreciated that any known cold plasma treatment method or surface modification method for implants suitable for use in accordance with the methods of this invention are contemplated herein and to be considered as part of this invention.

In one embodiment, the use of the solid substrates, processes and/or kits of this invention employ use of a coral. In one embodiment, the coral comprise any species, including, inter alia, *Porites, Acropora, Goniopora, Millepora*, or a combination thereof. In another embodiment the solid substrates, processes and/or kits of this invention employ use of nacre, molusc shell, or bone morsels.

In one embodiment, the coral is from the *Porites* species. In one embodiment, the coral is *Porites Lutea*. In one embodiment, the coral is from the *Acropora* species. In one embodiment, the coral is *Acropora grandis*, which in one embodiment is very common, fast growing, and easy to grow in culture. Thus, in one embodiment *Acropora* samples can be easily collected in sheltered areas of the coral reefs and collection from the coral reefs can be avoided by use of cultured coral material.

In another embodiment, the coral is from the *Millepora* species. In one embodiment, the coral is *Millepora dichotoma*. In one embodiment, the coral has a pore size of 150 µm and can be cloned and cultured, making Millerpora useful as a framework in the solid substrates, methods and/or kits of this invention.

In one embodiment, the coral is from the *Goniopora* species. In some embodiments, the coral is *Goniopora albiconus, Goniopora burgosi, Goniopora cellulosa, Goniopora ceylon, Goniopora ciliatus, Goniopora columna, Goniopora djiboutiensis, Goniopora eclipsensis, Goniopora fruticosa, Goniopora gracilis, Goniopora klunzingeri, Goniopora lobata, Goniopora mauritiensis, Goniopora minor, Goniopora norfolkensis, Goniopora palmensis, Goniopora pandoraensis, Goniopora parvistella, Goniopora pearsoni, Goniopora pendulus, Goniopora planulata, Goniopora polyformis, Goniopora reptans, Goniopora savignyi, Goniopora somaliensis, Goniopora stokes, Goniopora stutchburyi, Goniopora sultani, Goniopora tenella, Goniopora tenuidens* or *Goniopora viridis*.

In another embodiment, the coral is from any one or more of the following species *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora suharsonoi; Acropora chesterfieldensis; Acropora clathrata; Acropora cophodactyla; Acropora* sp. "danai-like"; *Acropora divaricata; Acropora donei; Acropora echinata; Acropora efflorescens; Acropora gemmifera; Acropora globiceps; Acropora granulosa; Acropora* cf *hemprichi; Acropora kosurini; Acropora* cf *loisettae; Acropora longicyathus; Acropora loripes; Acropora* cf *lutkeni; Acropora paniculata; Acropora proximalis; Acropora rudis; Acropora selago; Acropora solitaryensis; Acropora* cf *spicifera* as per Veron; *Acropora* cf *spicifera* as per Wallace; *Acropora tenuis; Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea collumna; Coscinaraea crassa; Cynarina lacrymalis; Distichopora violacea; Echinophyllia echinata; Echinophyllia* cf *echinoporoides; Echinopora gemmacea; Echinopora hirsutissima; Euphyllia ancora; Euphyllia divisa; Euphyllia yaeyamensis; Favia rotundata; Favia truncatus; Favites acuticollis; Favities pentagona; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipora platyphylla; Monastrea curta; Monastrea colemani; Montipora caliculata; Montipora capitata; Montipora foveolata; Montipora meandrina; Montipora tuberculosa; Montipora* cf *vietnamensis; Oulophyllia laevis; Oxypora crassispinosa; Oxypora lacera; Pavona bipartita; Pavona venosa; Pectinia alcicornis; Pectinia paeonea; Platygyra acuta; Platygyra pini; Platygyra* sp "green"; *Platygyra verweyi; Podabacia* cf *lanakensis; Porites annae; Porites cylindrica; Porites evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata*; or any coral known in the art, or a combination thereof.

In another embodiment, derivatives of marine animals—such as coral, sponges, moluscs shells and other related organisms may be used in the solid substrates, methods and/or kits of this invention may be Madreporaria, Helioporida of the order Coenothecalia, *Tubipora* of the order Stolonifera, *Millepora* of the order Milleporina, or others known in the art. In some embodiments, coral for use in the substrates, methods and/or kits of this invention may comprise scleractinian coral, including in some embodiments, *Goniopora* and others. In some embodiments, coral for use in the substrates, methods and/or kits of this invention may comprise Alveoppora. In some embodiments, coral for use in the substrates, methods and/or kits of this invention may comprise bamboo corals, including in some embodiments, coral from the family Isididae, genera Keratoisis, Isidella, and others.

In one embodiment of this invention, the term "coral" refers to coral which is cut from a single piece of coral.

In one embodiment, coral may be machined into the described configurations, and quite complex shapes which are substantially conical, but for example, further modified to include or be shaped to include a threaded structure is envisioned and the same may be formed by appropriate machine or other processing, such as chemical processing.

In some embodiments, the solid substrate is scaled into a size/dimension so as to be most approximate to accommodate a site of desired tissue growth or repair in terms of its width and length, while the height of same is such that upon implantation within underlying bone/cartilage interface results in the implant being at least 2 mm less than an articular cartilage layer surface or is proximal to a tide mark region in said implantation site.

In some embodiments, the solid substrate comprises a hollow or hollows along a Cartesian coordinate axis of said solid substrate, and the solid substrate is comprised of any suitable material.

In one embodiment, the length and/or width of solid substrates may be any that would be useful for the purposes of the present invention, as would be known to one of skill in the Art depending on the purpose. For example and in one embodiment, the solid substrate may be substantially the same length and/or width as the structure it is meant to replace, while in another embodiment, the solid substrate or a portion thereof may be the length and/or width of a defect, fissure or fracture such that it may be placed therein to enhance/replace tissue formation/function in a discrete location. According to these aspects, it will be understood that the sides of such implant may have a taper with respect to a longitudinal axis through such implant and that the height of same will be approximately 2 mm less than the articular cartilage surface proximal to the tissue site being treated.

In one embodiment, a solid substrate of this invention comprises an average void diameter, average pore size or a combination thereof appropriate for cell seeding and/or development of vasculature.

In one embodiment, when the solid substrate for use is coral, the coral is washed, bleached, frozen, dried, exposed to electrical forces, magnetic forces or ultrasound waves or microwaves or electromagnetic radiation or high pressure or a combination thereof prior to use thereof.

For example, and in some embodiments, solid substrates for use in osteochondral therapy or repair may make use of a substrate that has a diameter of about 5-15 mm, and a height of about 5-25 mm, however, implantation of same ensures that the height does not reach an articular surface layer of proximal to the tissue site being treated, and in some aspects, the height will be at least approximately 2 mm lower than such articular surface. In some embodiments, the solid substrate has a diameter of about 1-35 mm, and a height of about 1-45 mm however, implantation of same ensures that the height does not reach an articular surface layer of proximal to the tissue site being treated, and in some aspects, the height will be at least approximately 2 mm lower than such articular surface. In some embodiments, the solid substrate has a diameter of about 5-40 mm, such as, for example, 5, 10, 15, 20, 25, 30, 35, or 40 mm and a height of about 5-60 mm, such as, for example, 5, 10, 15, 20, 25, 30, 35, 49, 45, 50, 55 or 60 mm or a diameter of about 5-15 mm, and a height of about 5-45 mm however, implantation of same ensures that the height does not reach an articular surface layer of proximal to the tissue site being treated, and in some aspects, the height will be at least approximately 2 mm lower than such articular surface.

It will be appreciated by the skilled artisan that the size of the substrate may be so selected so as to be suitable to a particular application, for example, when using as a scaffolding material for bone repair, then the size may approximate the dimensions of a long bone in the subject. Accordingly, this invention is not to be limited by the size of the solid substrate.

It will be appreciated by the skilled artisan that the overall shape of the substrate may be so selected so as to be suitable to a particular application, for example, when using as a scaffolding material for condyle repair, then the shape may by curved in addition to being of the approximate dimensions of the regions of the condyle being repaired in the subject. Accordingly, this invention is not to be limited by the shape of the solid substrate.

In some embodiments, the coral for use in accordance with the instant invention may be prepared as described in PCT International Application publication Number WO 2009/066283, PCT International Application publication Number WO 2010/058400, PCT International Application publication Number WO 2010/146574 and PCT International Application publication Number WO 2010/146574, each of which is fully incorporated by reference herein, in its entirety.

A solid substrate of this invention is characterized by a specific fluid uptake capacity value as desired for the specific application for example of at least 75%, which specific fluid uptake capacity value is determined by establishing a spontaneous fluid uptake value divided by a total fluid uptake value.

In some embodiments, the fluid is a biologic fluid, which in some embodiments is blood, and in some embodiments, the biologic fluid is water. In some embodiments, the biologic fluid is hydrophilic. In some embodiments the fluid is a plasma or plasma-containing solution. In some embodiments, the fluid is a protein-containing or carbohydrate-containing solution. In some embodiments the fluid is a salt-containing solution. In some embodiments, the solution is a glycoprotein-containing solution.

In some embodiments, the biologic fluid is autologous with respect to a cell or tissue of a subject when said solid substrate is contacted with such cell or tissue of said subject.

In some embodiments, the biologic fluid is a blood analog as herein defined.

In some embodiments, surprisingly, it was found that a solution containing 40% glycerol and 1 g/L glucose in normal saline was a useful fluid for evaluation of the specific fluid uptake capacity values of the solid substrates as herein described. In some embodiments, such solution is referred to as a "blood analogue" as its biocompatibility and other desirable characteristics, such as viscosity for the purpose of evaluating the specific fluid uptake capacity values of the solid substrates as herein described provides values as consistently as when autologous or allogeneic blood is used, or water and therefore can serve as an analogue for such screening protocols.

In some aspects, reference to a blood analogue herein will be understood to specifically refer to any solution containing from about 20 to about 60% glycerol and 1 g/L glucose in normal saline.

In some aspects, such blood analogue may further comprise a color indicator or dye, such as FD&C blue #2 Aluminum lake dye or FD&C blue #2 dye, or any other appropriate color indicator, as will be appreciated by the skilled artisan. In some embodiments, the blood analogue will comprise 1 g/L FD&C blue #2 Aluminum lake dye, or in some embodiments, the blood analogue will further comprise 0.075 g/L FD&C blue #2 dye, as these are convenient concentrations for the color indicator. It will be appreciated by the skilled artisan that the color indicator may be provided at any convenient concentration that provides a desired detectable signal.

It will be appreciated by the skilled artisan that the fluid for use in determining specific fluid uptake capacity values of the solid substrates as herein described may include any appropriate described fluid, for example, Salt based solutions such as physiologic Saline (0.9% NaCl), or in some embodiments, Carbohydrate based solutions such as Glucose 1 g/L in saline, or in some embodiments, Glucose 1 g/L in WFI, or in some embodiments, Glucose 10 g/L in WFI, or in some embodiments, a Protein based solution such as BSA 50 g/L in saline, or in some embodiments, BSA 5 g/L in WFI, or in some embodiments, BSA 0.5 g/L in WFI, or in some embodiments, a Glycerol based solution, such as, for example, 22% Glycerol in saline, or in some embodiments, 22% Glycerol in WFI, or in some embodiments, 30% Glycerol in WFI, or in some embodiments, 44% Glycerol in WFI, or in some embodiments, a Xanthan-Gum & Glycerol solution, such as, for example, 0.025% Xanthan-Gum+30% Glycerol in WFI, or in some embodiments, combinations of the above, for example, Glycerol/Glucose/BSA/saline/Skim milk, or in some embodiments, Glucose 0.1 g/dL+BSA 5 g/dL in saline, or in some embodiments, 5 g/dL skim milk in saline, or in some embodiments, 22% Glycerol+50 g/L skim milk in saline, or in some embodiments, 22% Glycerol+10 g/L Glucose in saline, or in some embodiments, 22% Glycerol+1 g/L Glucose in saline, or in some embodiments, 30% Glycerol+1 g/L Glucose in saline, or in some embodiments, 30% Glycerol+10 g/L Glucose in saline, or in some embodiments, 32.5% Glycerol+1 g/L Glucose in saline, or in some embodiments, 35% glycerol+1 g/L Glucose in saline, or in some embodiments, 35% Glycerol+1 g/L Glucose in saline, or in some embodiments, 40% Glycerol+1 g/L Glucose in saline, or in some embodiments, PEG/Tween 20/Gelatin such as, for example, 40% Glycerol+1 g/L Glucose in saline+1% PEG, or in some embodiments, 40% Glycerol+1 g/L Glucose in saline+0.1% PEG, or in some embodiments, 40% Glycerol+1 g/L Glucose in saline+0.1% PEG+0.1% Tween 20, or in some embodiments, 40% Glycerol+1 g/L Glucose in saline+0.1% PEG+0.1% Gelatin, and others, as will be appreciated by the skilled artisan.

It will also be appreciated by the skilled artisan that any such fluid for use in determining the specific fluid uptake capacity values of the solid substrates as herein described may also be considered to represent an envisioned "blood analogue" as herein described.

It will be understood that any of the above are considered for use in determining the specific fluid uptake capacity values of the solid substrates as herein described and may in part function as a type of blood analogue for the purpose of such determination. In some aspects, as a preferred embodiment of a blood analogue as referred to herein, such analogue will comprise 40% glycerol and 1 g/L glucose in normal saline and optionally will further comprise a color indicator as herein described.

In some aspects, the blood analog as herein described will be further characterized by the following characteristics: having a density of approximately 1.12 g/mL; and having a viscosity of approximately 4.57 mPa/sec at 25° C.

It will be understood that the biologic fluid whose incorporation is appropriate within a solid substrate for the desired application.

In some embodiments, the process further comprises the step of contacting the material with a fluid for from 2-15 minutes to promote spontaneous fluid uptake of said fluid within said coralline-based solid material to arrive at said spontaneous fluid uptake value. In some embodiments, the process may allow for the contacting of the material with a fluid for from 0.5-15 minutes, or in some embodiments, from 0.5-5 minutes, or in some embodiments, 10-60 minutes, or in some embodiments, from 60 to 90 minutes, or in some embodiments, other intervals, to promote spontaneous fluid uptake. The skilled artisan will appreciate that the amount of time for which the fluid is applied to determine the spontaneous uptake may be extended or shortened as a function of the dimensions and geometry of the sample substrate being assessed. In some embodiments, when a larger sample is being assessed, the process further comprises the step of contacting the material with a fluid for from 2-24 hours to promote spontaneous fluid uptake of said fluid within said coralline-based solid material to arrive at said spontaneous fluid uptake value In some embodiments, the process further comprises the step of contacting said solid material with a fluid and applying negative pressure to the solid implant material to promote maximal uptake of said fluid within said coralline-based solid material to arrive at said total fluid uptake value. In some embodiments, application of positive pressure is via the application of a vacuum to the substrate immersed in the fluid, promoting entry of the fluid therewithin.

In some embodiments, the process may further comprise the step of contacting the solid implant material with a fluid and applying positive pressure to same to promote maximal uptake of fluid within the solid implant material to arrive at said total fluid uptake value. According to this aspect, and in some embodiments, care will be taken to ensure that the application of pressure does not in any way compromise the structural integrity of the solid substrate.

In some embodiments, application of positive pressure is via any manual means, for example, via the use of any applicator, syringe, etc., gravitational pressure, and others, as will be appreciated by the skilled artisan. In some embodiments, application of positive pressure is via forced osmosis, centrifugation and others. In some embodiments, combinations of the described methods and others are envisioned.

In some embodiments, the solid substrate for promoting cell or tissue growth or restored function comprises a coralline or coralline derivative, or other appropriate solid implant material characterized by having a contact angle value of less than 60 degrees, when in contact with a fluid.

Methods for determining a contact angle are well known, and any appropriate method can be used.

In some aspects, the sample is further dried under vacuum and/or heated or pressurized or steam treated.

In some embodiments, for aspects relating to a specific fluid uptake capacity value, such value is a function of change in weight in the solid implant material.

According to this aspect and in some embodiments, the dry weight for each sample is recorded and fluid as described herein is added an assay container.

According to this aspect and in some embodiments, at least 1:1 ratio of the size of the sample in mm to the volume of fluid added in ml is applied to the container. In some embodiments, the amount of fluid applied is in excess, as compared to the sample size.

According to this aspect and in some embodiments, once the initial fluid uptake is assessed, according to this aspect and in some embodiments, the solid substrate sample is then brought into contact with the fluid and the weight of the solid substrate sample is assessed. In other embodiments the specific gravity is assessed by gradient centrifugation of by the Archimedean principle.

According to this aspect and in some embodiments, spontaneous fluid uptake is assessed and a spontaneous fluid uptake value is established, based on the change in weight of the sample.

According to this aspect and in some embodiments, the specific fluid uptake capacity value is a function of change in fluid volume of applied fluid to said marine organism skeletal derivative-based solid material. According to this aspect, spontaneous fluid uptake is assessed and a spontaneous fluid uptake value is established based on the complete uptake of the volume applied to the sample.

According to this aspect and in some embodiments, the process then further comprises contacting a significantly increased amount of fluid with the sample and applying pressure thereto to promote maximal fluid uptake to the total fluid uptake capacity of the sample.

According to this aspect and in some embodiments, as noted, such pressure may be either positive or negative pressure, and the application time is for a period of time sufficient to ensure maximal uptake of the applied fluid into the marine organism skeletal derivative sample.

According to this aspect and in some embodiments, such time may include an interval of from 0.5-60 minutes, or in some embodiments, when a larger sample is being assessed, such time may include an interval of from 2-24 hours to arrive at said spontaneous fluid uptake value. It will be appreciated that the time intervals recited herein are applicable for any embodiment with regard thereto as described herein. The skilled artisan will appreciate that the amount of time for which the fluid is applied to determine the full capacity fluid uptake may be extended or shortened as a function of the dimensions and geometry of the sample substrate being assessed.

According to these aspects, the total fluid uptake capacity is thus assessed and the specific fluid uptake capacity value is then determined.

In some embodiments, the invention specifically contemplates solid substrates having a specific fluid uptake capacity value exceeding the cutoff value of 75%, for the sample to be noted optimized as a solid substrate for promoting cell or tissue growth. It will be appreciated that the invention contemplates the stated cutoff value for promoting a reasonable value that reduces the presence of appreciable false positives, i.e. solid substrates that are not as optimal for the stated applications.

In some embodiments, the invention specifically contemplates solid substrates characterized by having a contact angle value of less than 60 degrees, when in contact with a fluid, for the sample to be noted optimized as a solid substrate for promoting cell or tissue growth. It will be appreciated that the invention contemplates the stated cutoff value for promoting a reasonable value that reduces the presence of appreciable false positives, i.e. solid substrates that are not as optimal for the stated applications.

In some embodiments, samples thus processed and found to be characterized by a specific fluid uptake capacity value of at least 75%, or specific selection of organism skeletal derivative-based solid substrates characterized by having a contact angle value of less than 60 degrees, when in contact with a fluid may then be used for the isolation of proximally located regions of a section from which such sample was taken, which samples can then be reliably used and considered as being optimized in accordance with the processes of this invention. In some embodiments, with regard to coral-based samples, such regions may include the entire annual growth ring region within the coral from which the sample was derived.

In some embodiments, samples thus processed and found to be characterized by a specific fluid uptake capacity value of at least 75%, or specific selection of organism skeletal derivative-based solid substrates characterized by having a contact angle value of less than 60 degrees, when in contact with a fluid, may then be dried fully and utilized for implantation into a subject or for use as an ex-vivo substrate for cell or tissue growth for subsequent implantation and then machined into the described substantially conical shapes as characterized herein.

In some embodiments, when the sample is utilized in vivo in subsequent applications, in some aspects, the sample is first contacted with autologous biological fluids or materials from the host prior to implantation into the same, verifying the observed enhanced fluid uptake phenotype as herein described.

In one embodiment of this invention, the solid substrate may further comprise an additional material.

In some embodiments, such additional material may include a polymer, visco-supplement, hydrogel, and the like.

In some embodiments, such polymer may be applied apically to the solid substrate in situ and in some embodiments such polymer may form an apical layer over the solid substrate, filling the void created by the height of the substrate being approximately 2 mm below the articular cartilage layer proximal to the implantation site.

The term "polymer" refers, in some embodiments, to the presence of a layer of polymeric material in association with at least a portion of the solid substrate material. In some embodiments, such polymer layer is a coating for the solid substrate material.

In some embodiments, such coating may be over the entirety of the solid substrate, and in some embodiments, such coating may penetrate to within the voids and/or pores and/or hollows of the solid substrate. In some embodiments, such coating may be selectively applied to a particular region of the solid substrate, such that it creates a separate phase on the solid substrate, and in some embodiments, such polymer may be so applied that a thick polymer layer or phase is associated with a portion of a solid substrate, thereby creating a separate polymer phase in association with the solid substrate as herein described.

In one embodiment, the polymer coating provides added features to the solid substrates as herein described, for example, added tensile strength, added flexibility, reduced brittleness, and other attributes, to the solid substrate and in some embodiments, the polymer coating results in greater cellular attraction and attachment to the solid substrates as herein described, which in turn, inter alia, results in enhanced repair in terms of quantity, quality and timing of repair. In some embodiments, the polymer coating enhance cells proliferation and/or differentiation into desired mature tissue which in turn, inter alia, results in enhanced repair in terms of quantity, quality and timing of repair.

In one embodiment of this invention, a polymer coating is permeable. In one embodiment, the permeable polymer coating comprises a special porous membrane. In one embodiment, the term "permeable" refers to having pores and openings. In one embodiment, the permeable polymer coating of this invention has pores and openings which allow entry of nutrients, a therapeutic compound, a cell population, a chelator, or a combination thereof. In one embodiment, the permeable polymer coating of this invention has pores and openings which allow exit/release of nutrients, a therapeutic compound, a cell population, a chelator, or a combination thereof.

In one embodiment, a polymer coating of this invention is discontinuous. In one embodiment, a region or a plurality of sub-regions of the coral of this invention comprise an absence of polymer coating, allowing direct contact between the coral and the environment.

In some embodiments, the solid substrate incorporates a biocompatible polymer therewithin, which is associated with the aragonite or calcite component, via any physical or chemical association. In some embodiments, the polymer is a part of a hydrogel, which is incorporated in the solid substrates of this invention. In some embodiments, such hydrogel-containing solid substrates may thereafter be lyophilized or dessicated, and may thereafter be reconstituted.

In some embodiments of the solid substrates of this invention, the polymer may be applied to the solid substrate so as to form a separate phase, or in some embodiments, the polymer may be applied as a layer onto the solid substrate, or in some embodiments, the solid substrate may comprise both polymer as an internal or externally associated layer with a separate phase attached thereto comprising the same or a different polymeric material.

Such polymer-containing solid substrates may be particularly suited for cartilage repair, regeneration or enhancement of formation thereof. In some embodiments, according to this aspect, for example, in the treatment of osteochondral defects, the solid substrate is of a dimension suitable for incorporation within affected bone, and further comprises a polymer-containing phase, which phase, when inserted within the affected defect site, is proximal to affected cartilage. In another aspect and representing an embodiment of this invention, the solid substrate comprises a polymer, which has permeated within the voids and pores of the solid substrate, which solid substrate is inserted within a site of cartilage repair and which polymer facilitates cartilage growth, regeneration or healing of the defect site.

Such polymer-containing solid substrates may be particularly suited for bone repair, regeneration or enhancement of formation thereof. In some embodiments, according to this aspect, for example, in the treatment of bone edema, bone breakage or fragmentation, non union fractures, dental applications and maxillofacial applications, disease or defect, the coralline-based solid substrate is of a dimension suitable for incorporation within affected bone, and further comprises a polymer, which polymer has permeated within the voids and pores of the solid substrate, which solid substrate is inserted within the bone and which polymer facilitates bone growth, regeneration or healing of the defect site.

In one embodiment, a polymer coating of this invention comprises a natural polymer comprising, collagen, fibrin, elastin, silk, hyaluronic acid, sodium hyaluronate, cross linked hyalronic acid, chitosan, cross linked chitosan, alginate, calcium alginate, cross linked calcium alginate and any combinations thereof.

In one embodiment, the polymer comprises synthetically modified natural polymers, and may include cellulose derivatives such as alkyl celluloses, hydroxyalkyl celluloses, cellulose ethers, cellulose esters and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

In one embodiment, of this invention, a polymer comprises a synthetic biodegradable polymer. In one embodiment of this invention, a synthetic biodegradable polymer comprises alpha-hydroxy acids including poly-lactic acid, polyglycolic acid, enantioners thereof, co-polymers thereof, polyorthoesters, and combinations thereof.

In one embodiment, a polymer of this invention comprises a poly(cianoacrylate), poly(alkyl-cianoacrylate), poly (ketal), poly(caprolactone), poly(acetal), poly($\alpha$-hydroxy-ester), poly($\alpha$-hydroxy-ester), poly(hydroxyl-alkanoate), poly(propylene-fumarate), poly (imino-carbonate), poly(ester), poly(ethers), poly(carbonates), poly(amide), poly(siloxane), poly(silane), poly(sulfide), poly(imides), poly (urea), poly(amide-enamine), poly(organic acid), poly (electrolytes), poly(p-dioxanone), poly(olefin), poloxamer, inorganic or organomatallic polymers, elastomer, or any of their derivatives, or a copolymer obtained by a combination thereof.

In one embodiment, a polymer of this invention comprises poly(D,L-lactide-co-glycolide) (PLGA). In another embodiment, the polymer comprises poly(D,L-lactide) (PLA). In another embodiment, the polymer comprises poly(D,L-glycolide) (PGA). In one embodiment, the polymer comprises a glycosaminoglycan.

In one embodiment, the polymer comprises synthetic degradable polymers, which may include, but are not limited to polyhydroxy acids, such as poly(lactide)s, poly(glycolide)s and copolymers thereof; poly(ethylene terephthalate); poly(hydroxybutyric acid); poly(hydroxyvaleric acid); poly [lactide-co-($\epsilon$-caprolactone)]; poly [glycolide-co($\epsilon$-caprolactone)]; poly(carbonate)s, poly(pseudo amino acids); poly(amino acids); poly(hydroxyalkanoate)s; poly(anhydrides); poly(ortho ester)s; and blends and copolymers thereof.

In one embodiment of this invention, a polymer comprises proteins such as zein, modified zein, casein, gelatin, gluten, serum albumin, collagen, actin, $\alpha$-fetoprotein, globulin, macroglobulin, cohesin, laminin, fibronectin, fibrinogen, osteocalcin, osteopontin, osteoprotegerin, or others, as will be appreciated by one skilled in the art. In another embodiment, a polymer may comprise cyclic sugars, cyclodextrins, synthetic derivatives of cyclodextrins, glycolipids, glycosaminoglycans, oligosaccharides, polysaccharides such as alginate, carrageenan ($\chi$, $\lambda$, $\mu$, $\kappa$), chitosane, celluloses, condroitin sulfate, curdlan, dextrans, elsinan, furcellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, or a poly(3-hydroxyalkanoate)s, such as poly($\beta$-hydroxybutyrate), poly(3-hydroxyoctanoate) or poly(3-hydroxyfatty acids), or any combination thereof.

In one embodiment, the polymer comprises a bioerodible polymer such as poly(lactide-co-glycolide)s, poly(anhydride)s, and poly(orthoester)s, which have carboxylic groups exposed on the external surface as the smooth surface of the polymer erodes, which may also be used. In one embodiment, the polymer contains labile bonds, such as polyanhydrides and polyesters.

In one embodiment, a polymer may comprise chemical derivatives thereof (substitutions, additions, and elimination of chemical groups, for example, alkyl, alkylene, hydroxylations, oxidations, and other modifications routinely made by those skilled in the art), blends of, e.g. proteins or carbohydrates alone or in combination with synthetic polymers.

In one embodiment of this invention, the polymer is biodegradable. In one embodiment, the term "biodegradable" or grammatical forms thereof, refers to a material of this invention, which is degraded in the biological environment of the subject in which it is found. In one embodiment, the biodegradable material undergoes degradation, during which, acidic products, or in another embodiment, basic products are released. In one embodiment, bio-degradation involves the degradation of a material into its component subunits, via, for example, digestion, by a biochemical process. In one embodiment, biodegradation may involve cleavage of bonds (whether covalent or otherwise), for example in a polymer backbone of this invention. In another embodiment, biodegradation may involve cleavage of a bond (whether covalent or otherwise) internal to a side-chain or one that connects a side chain to, for example a polymer backbone.

In one embodiment, a solid substrate of this invention is covalently associated with the polymer coating via the use of a cross-linking agent. In one embodiment, the phrase "cross-linking agent" refers to an agent which facilitates the formation of a covalent bond between 2 atoms. In one embodiment, the cross-linking agent is a zero-length cross-linking agent.

In one embodiment, the cross-linking agent is (1 ethyl 3-(3dimethyl aminopropyl)carbodiimide (EDAC), N-Sulfohydroxy succinamide (Sulfo NHS), 5-iodopyrimidines, N-carbalkoxydihydroquinolines, pyrroloquinolinequinones, genipin or a combination thereof.

In one embodiment, the cross-linking agent is a homobifunctional cross-linker, such as, for example, a N-hydroxysuccinimide ester (e.g. disuccinimidyl suberate or dithiobis (succinimidylpropionate), homobifunctional imidoester (e.g. dimethyladipimidate or dimethyl pimelimidate), sulfhydryl-reactive crosslinker (e.g. 1,4-di-[3'-(2'-pyridyldithio) propionamido]butane), difluorobenzene derivative (e.g. 1,5-difluoro-2,4-dinitrobenzene), aldehyde (e.g. formaldehyde, glutaraldehyde), bis-epoxide (e.g. 1,4-butanediol diglycidyl ether), hydrazide (e.g. adipic acid dihydrazide), bis-diazonium derivative (e.g. o-tolidine), bis-alkylhalide, or a combination thereof.

In one embodiment, the cross-linking agent is a heterobifunctional cross-linker, such as, for example, an amine-reactive and sulfhydryl-reactive crosslinker (e.g. N-succinimidyl 3-(2-pyridyldithio)propionate, a carbonyl-reactive and sulfhydryl-reactive crosslinker (e.g. 4-(4-N-maleimidophenyl)butyric acid hydrazide), or a combination thereof.

In some embodiments, the cross-linking agent is a tri-functional cross-linkers, such as, for example, 4-azido-2-nitrophenylbiocytin-4-nitrophenyl ester, sulfosuccinimidyl-2-[6-biotinamido]-2-(p-azidobenzamido)hexanoamido] ethyl-1,3'-dithiopropionate (sulfo-SBED), or a combination thereof.

In another embodiment, the cross-linking agent is an enzyme. In one embodiment of this invention, the cross-linking agent comprises a transglutaminase, a peroxidase, a xanthine oxidase, a polymerase, or a ligase, or a combination thereof.

The choice of concentration of the cross-linking agent utilized for activity will vary, as a function of the volume, agent and polymer chosen, in a given application, as will be appreciated by one skilled in the art.

In one embodiment, the association of a solid substrate of this invention with a polymer coating of this invention comprises a physical and/or mechanical association. For example, in one embodiment, a physical and/or mechanical association may comprise imbibing of any means, air drying, using a cross-linking agent, applying of heat, applying vacuum, applying lyophilizing methods, freezing, applying mechanical forces or any combination thereof, to promote the physical association between a coral and a polymer coating as described herein.

In some embodiments, the choice of polymer, or application of polymer to a solid substrate as herein described may be so chosen, for an added ability to increase fluid uptake. Similarly, the surface of the solid substrate may be treated to increase fluid uptake therewithin, as well. In some embodiments, such surface treatment may include application of plasma to the solid substrate.

It will be apparent to one skilled in the art that the physical and/or chemical properties of a polymer application to a solid substrate of this invention and components thereof may influence methods of use of this invention and kits thereof, for inducing or enhancing cartilage and/or bone repair.

In one embodiment, the polymer as applied to the solid substrates of this invention has a thickness of between 2.0 µm and 0.1 µm. In one embodiment, the polymer coating has a thickness of about 1.0 µm. In one embodiment, the polymer coating of this invention has a thickness of between 10 µm and 50 µm. In one embodiment, the polymer coating as applied to the solid substrates of this invention has a thickness of about 10-25, or about 15-30, or about 25-50 µm. In one embodiment, the polymer coating as applied to the solid substrates of this invention has a thickness of about 0.0001-0.1 µm. In one embodiment, the polymer coating as applied to the solid substrates of this invention has a thickness of about 20-200 µm. In one embodiment, the polymer coating as applied to the solid substrates of this invention has a thickness of about 100-1500 µm. In one embodiment, the polymer coating as applied to the solid substrates of this invention has a thickness of about 0.1-1.5 mm or 1-3 mm or 2-7 mm.

In some embodiments, the polymer as applied to the solid substrates of this invention is a thin coating, which is associated with the solid substrates of this invention and has a thickness as indicated hereinabove.

In some embodiments, the polymer as applied to the solid substrates of this invention is applied throughout the solid substrates of this invention, such that, in some embodiments, the pores and voids within the solid substrates of the invention may be filled with polymers as herein described, and such polymer layer as applied may have a thickness of about 60-900 µm.

In some embodiments, the polymer is applied to an apical surface of an implant, in situ, as part of an implantation procedure of this invention.

In some embodiments, the polymer as applied to the solid substrates of this invention is to a terminus or a portion of the coating forming an additional polymer phase on the solid substrates of the invention. According to this aspect, and in some embodiments, the polymer layer as applied will have a thickness of between about 0.1-10 mm.

In some embodiments, multiple solid substrates comprising polymeric additives are implanted into a desired implantation site, wherein the polymer thickness applied to a first solid substrate may vary as compared to a polymer thickness as applied to a second solid substrate, implanted in the desired site. Variations in such thickness may reflect the range described herein.

In one embodiment, the thickness of the polymer as applied to the solid substrates of this invention influences physical characteristics of a solid substrate of this invention. For example, the thickness of a polymeric application may influence elasticity, tensile strength, adhesiveness, or retentiveness, or any combination thereof of a solid substrate of this invention. In one embodiment, the polymer application increases the elasticity of a solid substrate of this invention. In one embodiment, a polymeric application increases the tensile strength of a solid substrate of this invention. In one embodiment, the adhesiveness of a polymeric application relates to adhesion of mesenchymal stem cells, blood vessels, tissue at a site of desired repair, including cartilage repair, cartilage tissue, or bone tissue, or a combination thereof. In one embodiment, a polymeric application decreases the adhesiveness of a solid substrate of this invention. In one embodiment, a polymeric application increases the adhesiveness of a solid substrate of this invention. One skilled in the art will recognize that a polymeric application may increase adhesiveness for an item while decreasing adhesiveness for another item. For example, in one embodiment, the polymeric application increases adhesiveness for a mesenchymal stem cell and decreases adhesiveness of an infective agent. In one embodiment, the retentiveness of a polymeric application relates to retention of a cell population. In one embodiment, the cell population retained within a polymer coating is a mesenchymal stem cell population, chondrocyte population osteoblast population, etc. In one embodiment, the retentiveness of a polymeric application relates to retention of effector compounds.

In one embodiment, the thickness of the polymeric application influences proliferation and/or differentiation of cells applied to the solid substrates of this invention, or influences the activation or migration of cells associated with cell or tissue growth/restored function to the substrates of this invention, or a combination thereof.

Incorporation of a biocompatible polymer such as hyaluronic acid within a solid substrate of this invention may be accomplished via any means, including, in some embodiments, pressure-driven application, for example, via application under vacuum, centrifugal force or mechanical pressure. In some embodiments, gravitational force is sufficient to allow appropriate and relatively homogenous penetration of the hyaluronic acid to a desired depth of the implant. According to this aspect, in one embodiment, visual inspection of the implant, for example using the staining with Fast Green/Safranin O, demonstrates uniform distribution of the hyaluronic acid through the substrate to a desired depth as a function of the time and conditions of application.

In one embodiment, the solid substrates of this invention may further comprise an effector compound, which in some embodiments, may be associated directly with the solid substrates of this invention, or in some embodiments, may be associated with a polymer, and applied in connection therewith.

In one embodiment, such effector compounds might include silver ions, copper ions or other metals, or combinations thereof. In another embodiment release of this compound might be facilitated by the application of electrical charge.

In another embodiment a first implant may be coated with a metal such as silver and a second implant may be coated with a second metal such as gold. Application of electrical field or actuation by battery might cause an electrical charge to flow between the implanted materials and lead to sterilization of the area due to discharge of silver ions. Such implementation might, for example, be useful in the treatment of osteomyelitis.

In some aspects, coatings with any osteoconductive material are envisioned, such as, for example, hydroxyapatite, titanium, calcium phosphate biomaterials, or coatings as described by Goodman S B et. al., Biomaterials. 2013 April; 34(13): 3174-3183, or Zhang, B. G. X. et. al. Int J Mol Sci. 2014 July; 15(7): 11878-11921, both of which are incorporated herein by reference in their entirety.

In one embodiment, the effector compound comprises a component of a kit of this invention for use for incorporation into a solid substrate of this invention as herein described.

In one embodiment of this invention, the effector compound comprises a cytokine, a bone morphogenetic protein (BMP), growth factors, a chelator, a cell population, viscosupplement, platelet-rich plasma (PRP), stem cells, a therapeutic compound, or an antibiotic, or any combination thereof.

In one embodiment of this invention, the phrase "a therapeutic compound" refers to a peptide, a protein or a nucleic acid, or a combination thereof. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses. In one embodiment, the therapeutic compound comprises a pro-angiogenic factor.

In one embodiment, the effector compound comprises, an anti-helminth, an antihistamine, an immunomodulatory, an anticoagulant, a surfactant, an antibody, a beta-adrenergic receptor inhibitor, a calcium channel blocker, an ace inhibitor, a growth factor, a hormone, a DNA, an siRNA, or a vector or any combination thereof.

In one embodiment, the phrase "effector compound" refers to any agent or compound, which has a specific purpose or application which is useful in the treatment, prevention, inhibition, suppression, delay or reduction of incidence of infection, a disease, a disorder, or a condition, when applied to the solid substrates, kits and/or methods of this invention. An effector compound of this invention, in one embodiment, will produce a desired effect which is exclusive to the ability to image the compound. In some embodiments, the effector compound may be useful in imaging a site at which the compound is present, however, such ability is secondary to the purpose or choice of use of the compound.

In one embodiment of this invention, term "effector compound" is to be understood to include the terms "drug" and "agent", as well, when referred to herein, and represents a molecule whose incorporation within the solid substrate and/or kits of this invention, or whose use thereof, is desired. In one embodiment, the agent is incorporated directly within a solid substrate, and/or kit of this invention. In another embodiment, the agent is incorporated within a solid substrate and/or kit of this invention, either by physical interaction with a polymer coating, a coral, or coral particles of this invention, and/or a kit of this invention, or association thereto.

In one embodiment, the "effector compound" is a therapeutic compound.

In one embodiment, the phrase "a therapeutic compound", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the therapeutic compound may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P, transcription factors or combinations thereof.

In any of the embodiments herein, solid substrates, and their use in the methods of the present invention may further comprise, or be implanted with, other compounds such as, for example, antioxidants, growth factors, cytokines, antibiotics, anti-inflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-α), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

In any of the embodiments herein, solid substrates, and their use in the methods of the present invention may further comprise, or be implanted with, plasma, platelet rich plasma, any growth factor as appropriate, any glycosaminoglycan, in particular, hyaluronic acid and any useful form of same, or any combination of same.

In one embodiment, effector compounds for use in a solid substrate and/or a kit of this invention and/or a method of this invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, or a targeting moiety, or any combination thereof.

In one embodiment, the solid substrates and/or kits of this invention and/or methods of this invention comprise or make use of an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The solid substrates and/or kits of this invention and/or methods of use of this invention may comprise nucleic acids, in one embodiment, or in another embodiment, the solid substrates and/or kits of this invention and/or methods of use of this invention may include delivery of the same, as a part of a particular vector. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

In one embodiment, effector compounds for use in a solid substrate and/or a kit of this invention and/or a method of this invention may comprise, inter-alia, a cytokine, a bone morphogenetic protein (BMP), growth factor, a chelator, a cell population, a therapeutic compound, an anti-inflammatory compound, a pro-angiogenic compound or an antibiotic, or any combination thereof.

It will be appreciated that the solid substrates as herein described, and including any embodied addition to/incorporation within same, refers to such substrates possessing tapered sides as herein described, or in some embodiments, specifically shaped to be substantially ovoid in shape and optionally further comprising a taper, as described herein.

In some embodiments, the solid substrates of this invention may be seeded with cells, cell populations or tissue, pre-operative, intra operative or post-operative.

In some embodiments, the cells or tissue comprise stem or progenitor cells, or a combination thereof.

It will be appreciated that any appropriate stem or progenitor cell, from any source or obtained via any protocol is envisioned.

In some embodiments, adipose tissue derived stem cells are specifically envisioned for use in the methods of this invention and for incorporation with the solid substrates of this invention or kits of this invention.

In one embodiment of this invention, the cells or tissue as used in accordance with the substrates, methods of use or kits of this invention, are engineered to express a desired product.

In one embodiment, the phrase "a cell population" refers to a transfected cell population, a transduced cell population, a transformed cell population, or a cell population isolated from a subject, or a combination thereof. In some embodiments, transfected, transduced or transformed cells, may be seeded on the solid substrate, or in some embodiments, may be incorporated into a polymeric application thereto, or a combination thereof.

In one embodiment, a cell population of this invention comprises mesenchymal stem cells. In one embodiment, the mesenchymal stem cells are transformed.

In one embodiment, a cell population comprises cells beneficial in repair of a tissue for which the implantation of a solid substrate of this invention is desired.

In some embodiments, the cells are beneficial in and/or promote cartilage and/or bone formation and/or repair. Such cells may include chondroblasts or chondrocytes; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. The precursor cells for use in the method of the present invention are prepared from an organ tissue of the recipient mammal (i e autologous), or a syngeneic mammal. In another embodiment, allogeneic and xenogeneic precursor cells may be utilized.

In one embodiment, the solid substrate of this invention incorporates stem or progenitor or precursor cells. Such cells can be obtained directly from a mammalian donor, e.g., a patient's own cells, from a culture of cells from a donor, or from established cell culture lines. In some embodiments, the mammal is a mouse, rat, rabbit, guinea pig, hamster, cow, pig, horse, goat, sheep, dog, cat, monkey, ape or a human. Cells of the same species and/or of the same immunological profile can be obtained by biopsy, either from the patient or a close relative. Using standard cell culture techniques and conditions, the cells are then grown in culture until confluent and used when needed. The cells may be cultured until a sufficient number of cells have been obtained for a particular application.

In one embodiment, the solid substrate of this invention incorporates any cell which may participate in tissue repair, for example, in cartilage and/or bone formation or repair. In some embodiments, such cells represent autografts, in that cells are cultured ex-vivo to seed the cells on the solid substrates of the invention, and such seeded solid substrates are implanted into the subject.

In some embodiments, such cells may represent allografts or xenografts, which may be incorporated within the solid substrates of this invention and implanted within a site of repair.

In one embodiment, an implant of this invention comprises a cell population from a culture for a time period sufficient to seed the cells implant pre-operative, intra operative or post-operative. In one embodiment, the cell population is a mesenchymal stem cell population, chondrocyte; fibrochondrocyte; osteocyte; osteoblast; osteoclast; synoviocyte; bone marrow cell; stromal cell; stem cell; embryonic stem cell; precursor or stem cell derived from adipose tissue; peripheral blood progenitor cell; stem cell isolated from adult tissue; genetically transformed cell; or a combination thereof. In one embodiment, the mesenchymal stem cells; chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof seeded in vitro are transformed. In one embodiment, the cell population comprises a cell population beneficial for cartilage repair. In one embodiment, the culture comprises a chelator. In one embodiment of this invention, the chelator in a culture comprises a calcium chelator.

In some embodiments, the solid substrate may further serve as a bone substitute or bone void filler. In some embodiments, the solid substrate may further incorporate a bone-substitute or bone void filler. In some embodiments, such bone-containing material may comprise autologous or allogeneic bone. In some embodiments, such bone-containing material may comprise animal bone.

This invention provides the unexpected superior healing when application of optimally selected solid substrates useful in cell and tissue growth and/or restored function are specifically implanted within a site of tissue repair, whereby the solid substrate is substantially in a press fit/fight fit with respect to the length and width of the implantation site, yet the height of the solid substrate is approximately 2 mm below the articular cartilage layer in cartilage tissue proximal to the site of implantation. FIG. 3A-3C specifically demonstrates improved healing and articular cartilage regeneration at the apical region above the implantation site, as a consequence of the methods of implantation as described and exemplified herein.

In particular, this invention provides the unexpected application that bone regeneration, repair and enhancement of formation is optimal when the solid substrate is characterized by being implanted within a site of tissue repair, whereby the solid substrate is substantially in a press fit/fight fit with respect to the length and width of the implantation site, yet the height of the solid substrate is approximately 2 mm below the articular cartilage layer in cartilage tissue proximal to the site of implantation.

In other embodiments, this invention provides the unexpected advantage in terms of greater chondrogenesis, when the solid substrate is characterized by being implanted within a site of tissue repair, whereby the solid substrate is substantially in a press fit/tight fit with respect to the length and width of the implantation site, yet the height of the solid substrate is approximately 2 mm below the articular cartilage layer in cartilage tissue proximal to the site of implantation.

In some embodiments, solid substrates of this invention may be applied for use in a subject with a bone defect in need of repair, wherein access to the bone defect results in the creation of a defect in the overlying cartilage, and the solid substrates of this invention allow for ideal healing of affected bone or bone and cartilage tissues when the procedure for addressing same is characterized by a solid substrate for repair of same is being implanted within a site of tissue repair, whereby the solid substrate is substantially in a press fit/tight fit with respect to the length and width of the implantation site, yet the height of the solid substrate is approximately 2 mm below the articular cartilage layer in cartilage tissue or leveled with the tidemark proximal to the site of implantation.

In other embodiments, such solid substrates may be administered to a subject with a cartilage defect in need of repair, wherein optimal insertion of the solid substrate for stimulation of cartilage repair necessitates anchoring of the scaffold in the underlying bone, for example, by creating a minimal void in the underlying bone for insertion of the solid substrates, and is further characterized by implantation within a site of tissue repair is such, whereby the solid substrate is substantially in a press fit/tight fit with respect to the length and width of the implantation site, yet the height of the solid substrate is approximately 2 mm below the articular cartilage layer in cartilage tissue proximal to the site of implantation.

In other embodiments, such solid substrate may be administered to a subject with an osteochondral defect, where both bone and cartilage tissue are in need of repair as part of the pathogenesis of the disorder. The methods/substrates for use according to this aspect are, in some embodiments, particularly suited for such applications.

It will be appreciated by the skilled artisan, that the applications, in particular, as related to bone therapy may include use of a solid substrate that incorporates any additional element as described herein, including, for example, bone allograft, bone autograft, bone substitutes, known bone void fillers, therapeutic compounds, and the like.

In some embodiments, the solid substrates of this invention may be used in conjunction with other known and/or available materials for stimulating/enhancing cell and/or tissue growth and/or restored function, for example, by promoting bone and/or cartilage repair, and the methods of implantation utilize solid substrates incorporating same.

It is to be understood that any use of the solid substrates of this invention, alone or in conjunction with other appropriate materials, for the treatment, repair or stimulation of cell or tissue growth or restored function is to be considered as part of this invention, when implantation methods are characterized by implantation within a site of tissue repair involving the solid substrate implanted substantially in a press fit/fight fit with respect to the length and width of the implantation site, yet the height of the solid substrate is approximately 2 mm below the articular cartilage layer in cartilage tissue, or leveled with the tidemark, proximal to the site of implantation.

It will be appreciated that the solid substrates of this invention may be of any suitable size to accommodate its application in accordance with the methods of this invention. For example, and in some embodiments, for applications of the solid substrates of this invention within long bones of a subject, the dimensions of the solid substrate will be scaled to approximate that of the site into which the scaffold will be implanted, and may be on an order of magnitude scaling from millimeters to centimeters, as needed, characterized by the substrate being implanted within a site of tissue repair, whereby the solid substrate is substantially in a press fit/tight fit with respect to the length and width of the implantation site, yet the height of the solid substrate is approximately 2 mm below the articular cartilage layer in cartilage tissue proximal to the site of implantation.

This invention provides, in some embodiments, solid substrates for use in repairing cartilage and/or bone tissue defects associated with physical trauma, or cartilage and/or bone tissue defects associated with a disease or disorder in a subject.

In some aspects, it is particularly contemplated that the methods, solid substrates, kits and tools and systems of the invention are suitable for hip replacement, great toe fusion, arthrodesis, ankle replacement or fusion, total or partial knee replacement procedures, including any or all of same.

In some embodiments, multiple solid substrates as herein described are inserted to maximally occupy a defect site, to accommodate proper insertion into the desired region within a desired implantation site, in terms of length and width, and further characterized by insertion within a site of tissue repair, whereby the solid substrate is substantially in a press fit/fight fit with respect to the length and width of the implantation site, yet the height of the solid substrate is approximately 2 mm below the articular cartilage layer in cartilage tissue, or leveled with the tidemark, proximal to the site of implantation.

In some embodiments, this invention provides a method for optimal implantation of a solid substrate for promoting cell or tissue growth or restored function in an osteochondral, bone or cartilage tissue in a subject in need thereof, said method comprising:

selecting and preparing a solid substrate for promoting cell or tissue growth or restored function for implantation, which solid substrate has a length and width or that promotes a tight fit within the boundaries of the implantation site and is further characterized by a height sufficient such that when a first terminus of said solid substrate is implanted at or substantially proximal to a tide mark in a bone in a site for implantation, a second terminus of said solid substrate is at a height substantially 2 mm less than an articular cartilage layer surface, or leveled with the tidemark;

implanting said selected and prepared solid substrate within a site for implantation to span a basal to apical long axis of said site for implantation, wherein a first terminus of said implant is implanted within a bone at the basal surface and a second terminus is oriented apically such that said second terminus is at a height at least 2 mm less than an articular cartilage layer surface or is proximal to a tide mark region in said implantation site; and optionally applying a biocompatible polymer layer to an apical surface of said implant, filling the empty void to the level of articular cartilage surface in height.

In some embodiments, the substrate has a height of between 1-18 mm, and in some embodiments, the solid substrate has a height of between 5 and 10 mm. In some embodiments, the solid substrate has a diameter of about 1-35 mm.

In some embodiments, the methods of this invention include implantation of more than one solid substrate in a tissue site as described, and in some aspects, care is taken such that the two implanted substrates are implanted such that the first terminus is implanted within bone and the second terminus of each substrate is oriented to be at a height at least 2 mm less than an articular cartilage layer surface or is proximal to a tide mark region in said implantation site, as described, where there is a distance of at least 2 mm between the two substrates being implanted in the tissue site, so that each implant is fully surrounded by bone.

In some embodiments, the methods/solid substrates for use in accordance with this invention promotes cell or tissue growth or restored function in tissue a subject afflicted with a defect or disorder or disease of the cartilage or bone or a combination thereof. In some embodiments, the cartilage defect or disorder or disease comprises a full or partial thickness articular cartilage defect; osteochondral defect; osteoarthritis; avascular necrosis; osteochondritis dissecans; bone cyst, non-union fractures; a joint defect or a defect resulting from trauma, sports, or repetitive stress. In some embodiments, the defect or disorder or disease of the bone comprises a fracture, bone defect, bone edema, osteoporosis, or a defect resulting from trauma, sports, or repetitive stress. In some embodiments, the method reduces the incidence or extends the time or need for joint replacement in an affected subject. In some embodiments, the method serves to resurface an affected joint in a subject.

In one embodiment, the phrase "cartilage repair" refers to restoring a cartilage defect to a more healthful state. In one embodiment, restoring cartilage results in regeneration of cartilage tissue. In one embodiment, restoring cartilage results in regeneration of a full or partial thickness articular cartilage defect. In one embodiment, restoring cartilage results in complete or partial regeneration of cartilage tissue at a site of cartilage repair. In one embodiment, cartilage repair may result in restoration/repair of missing or defective bone tissue, wherein repair of a cartilage defect necessitates removal of bone tissue at a site of cartilage repair. In one embodiment, restoring cartilage results in regeneration of osteochondral defect. In one embodiment, cartilage repair comprises restoring cartilage defects of joints (e.g. knee, elbow, wrist, ankle, toe, finger, hip, shoulder joints), of ears, of a nose, or of a wind pipe, disc.

In one embodiment, the phrase "bone repair" refers to restoring a bone defect to a more healthful state. In one embodiment, restoring bone results in regeneration of bone tissue. In one embodiment, restoring bone results in the filling in of any fracture or void within a bone tissue. In one embodiment, restoring bone results in complete or partial regeneration of bone tissue at a site of bone repair. In one embodiment, bone repair may result in restoration/repair of missing or defective bone tissue. In one embodiment, bone repair comprises restoring bone defects of any bone, treating bone edema, avascular necrosis, osteochondritis dissecans, bone cyst, non-union fractures, and other bone disorders, as needed.

In some embodiments, the phrase "bone repair" refers to the treatment of a subject with osteoporosis, Paget's disease, fibrous dysplasias, bone edema or osteodystrophies. In another embodiment, the subject has bone and/or cartilage infirmity. In another embodiment, the subject has other bone remodeling disorders include osteomalacia, rickets, rheumatoid arthritis, achondroplasia, osteochodrytis, hyperparathyroidism, osteogenesis imperfecta, congenital hypophosphatasia, fribromatous lesions, multiple myeloma, abnormal bone turnover, osteolytic bone disease, periodontal disease, or a combination thereof. In one embodiment, bone remodeling disorders include metabolic bone diseases which are characterized by disturbances in the organic matrix, bone mineralization, bone remodeling, endocrine, nutritional and other factors which regulate skeletal and mineral homeostasis, or a combination thereof. Such disorders may be hereditary or acquired and in one embodiment, are systemic and affect the entire skeletal system.

In other aspects, the invention specifically contemplates use of the solid substrates as herein described and methods for use of same for treating a bone and/or cartilage defect arising as a consequence of tumor or avascular necrosis.

The solid substrates and/or kits for use and methods of the invention may also be used to enhance bone and/or cartilage formation in conditions where a bone and/or cartilage deficit is caused by factors other than bone remodeling disorders. Such bone deficits include fractures, bone trauma, conditions associated with post-traumatic bone surgery, post-prosthetic joint surgery, post plastic bone surgery, bone chemotherapy, post dental surgery and bone radiotherapy. Fractures include all types of microscopic and macroscopic fractures. In one embodiment, some examples of fractures includes avulsion fracture, comminuted fracture, transverse fracture, oblique fracture, spiral fracture, segmental fracture, displaced fracture, impacted fracture, greenstick fracture, torus fracture, fatigue fracture, intraarticular fracture (epiphyseal fracture), closed fracture (simple fracture), open fracture (compound fracture) and occult fracture. In one embodiment, fractures meant to be treated using the methods of the present invention are non-union fractures.

In one embodiment, the solid substrates and/or kits for use and methods of the invention may also be utilized for induced or enhanced repair of a cartilage and/or bone defect or disorder or disease. In one embodiment, the cartilage defect results from a trauma, a tear, a sports injury, a full thickness articular cartilage defect, a joint defect, or a repetitive stresses injury (e.g., osteochondral fracture, secondary damage due to cruciate ligament injury). In one embodiment, the cartilage disorder comprises a disease of the cartilage. In one embodiment, methods of this invention induce or enhance cartilage repair in osteoarthritis, rheumatoid arthritis, aseptic necrosis, osteoarthritis, including osteochondritis dissecans, articular cartilage injuries, chondromalacia patella, chondrosarcoma, chondrosarcoma-head and neck, costochondritis, enchondroma, hallux rigidus, hip labral tear, osteochondritis dissecans, torn meniscus, relapsing polychondritis, canine arthritis, fourth branchial arch defect or cauliflower ear. In one embodiment, methods of this invention induce or enhance cartilage repair in degenerative cartilagenous disorders comprising disorders characterized, at least in part, by degeneration or metabolic derangement of connective tissues of the body, including not only the joints or related structures, including muscles, bursae (synovial membrane), tendons, and fibrous tissue, but also the growth plate, meniscal system, and intervertebral discs.

In one embodiment, methods, materials and kits of this invention are utilized for resurfacing joints and in some embodiments, the methods, materials and kits of this invention in use as described herein, prevent, reduce the need, delay the need or abrogate the need for joint replacement.

In one embodiment, the solid substrates, kits and methods of the invention may also be used to augment long bone fracture repair; generate bone in segmental defects; provide a bone graft substitute for fractures; facilitate tumor reconstruction or spine fusion; provide a local treatment (by injection) for weak or osteoporotic bone, such as in osteoporosis of the hip, vertebrae, or wrist, or a combination thereof. In another embodiment, the solid substrates, kits and methods of the invention may also be used in a method to accelerate the repair of fractured long bones; treat of delayed union or non-unions of long bone fractures or pseudoarthrosis of spine fusions; induce new bone formation in avascular necrosis of the hip or knee, or a combination thereof.

In some embodiments, the solid substrates, kits and methods of the invention may also be used as an alternative, or in order to delay, full or partial joint replacement, for any bone as herein described, e.g. hip, knee, shoulder, elbow, ankle, and others as will be appreciated by the skilled artisan.

In one embodiment, methods of this invention are evaluated by examining the site of cartilage and/or bone tissue repair, wherein assessment is by histology, histochemistry, palpation, biopsy, endoscopy, arthroscopy, or imaging techniques comprising X-ray photographs, computerized X-ray densitometry, computerized fluorescence densitometry, CT, MRI or another method known in the art, or any combination thereof.

In one embodiment, a method of this invention comprises inducing and enhancing cartilage and/or bone repair wherein implanting a solid substrate of this invention as described within a site of cartilage and/or bone repair influences and improves cartilage and/or bone repair.

In one embodiment, a method of this invention induces or enhances cartilage and/or bone repair, wherein the solid substrate attracts a population of cells to the solid substrate, thereby influencing or improving cartilage and/or bone repair.

A clinician skilled in the art will recognize that methods of this invention, which entail implanting a solid substrate within a site of cartilage and/or bone repair, may require preparation of a site of cartilage and/or bone repair to enable insertion of same within bone, as herein described, to ensure the height of the substrate implanted is at least 2 mm less than an articular cartilage layer surface or is proximal to a tide mark region in said implantation site.

These preparations may occur prior to implantation of a coralline solid substrate or simultaneously with implantation. For example, cartilage and/or bone tissue and/or other tissues proximal to a site of cartilage and/or bone repair may initially be drilled through to create a channel of dimensions appropriate for a coralline solid substrate used in the methods of this invention. Then the coralline solid substrate is implanted within the site so that a region of the coralline solid substrate penetrates the drilled cartilage and/or bone tissues. Alternatively, the coralline solid substrate may be attached to a tool capable of penetrating through cartilage and/or bone or other tissues, or a combination thereof. In this case, as the tool penetrates through the cartilage and/or bone tissue, the attached coralline solid substrate is simultaneously implanted.

In some embodiments, following implantation of the solid substrate within a repair site, or several solid substrates within the repair site, the solid substrate is processed to optimize incorporation and optimal cartilage and/or bone repair. In some embodiments, such processing may comprise cutting, sanding or otherwise smoothing the surface of the solid substrate or coralline solid substrates, for optimal repair. According to this aspect, and in some embodiments, part of the processing ensures that the region of the substrate located in the cartilage phase, will nonetheless have a maximal height of at least 2 mm below the articular cartilage surface layer, or leveled with the tidemark, proximal to the site of implantation.

It will be appreciated that any of the methods and/or uses of the invention and/or implanted substrates and/or tools for use with same as described herein may be for human or veterinary use.

In some embodiments, the invention provides a method for implantation of an optimized solid substrate for promoting cell or tissue growth or restored function in a subject in need thereof, said method comprising:

Isolating or preparing an optimized solid substrate for promoting cell or tissue growth or restored function, which solid substrate comprises a coral or coral derivative, is characterized by a specific fluid uptake capacity value of at least 75%, or is characterized by having a contact angle value of less than 60 degrees and which is further characterized by a substantially conical shape, having a circular cross section at each end of said solid substrate and tapered sides;

establishing a specific fluid uptake capacity value of said solid substrate, which specific fluid uptake capacity value is determined by establishing a spontaneous fluid uptake value divided by a total fluid uptake value;

selecting a solid substrate characterized by a specific fluid uptake capacity value of at least 75% or is characterized by having a contact angle value of less than 60 degrees; and implanting said solid substrate characterized by a specific fluid uptake capacity value of at least 75% or is characterized by having a contact angle value of less than 60 degrees within a desired site in a subject, wherein said implanting is conducted at an implant angle of 2 degrees from an axis perpendicular to the surface of the tissue site being thus treated and wherein said implanting is conducted such that a gap between the articular cartilage layers on either side of the implanted substrate is created, such that an apex of said solid substrate is about 2 mm below the articular cartilage layer.

In the practice of the methods as herein described, in some embodiments, the invention provides a kit comprising one or more implants as herein described and in some embodiments, such kits may comprise a full complement of implants as herein described and tools for the implantation of same, as needed/desired.

In some embodiments, such kits will comprise any complement of solid substrates as herein described and optionally, may further comprise any biocompatible polymer as herein described, and hyaluronic acid is in particular envisioned in this context.

This invention specifically contemplates customized applications, wherein a solid substrate for implantation is specifically prepared in a customized manner to best fit a defect site in a subject in need of implantation of same, with the height of the implant thus constructed to be about 2 mm below the articular cartilage surface, or leveled with the tidemark, of tissue proximal to the site of the implantation.

In some aspects, this invention specifically contemplates that customization, in particular, with respect to implantation procedures within a curved tissue site in a subject include idealized preparation of a solid substrate for implantation, for example, via compiling information from a variety of sources such as MRI and/or CT scans, such that a plurality of medical images of a bone region with a defect area are obtained and converted into three-dimensional data.

In some aspects, such three-dimensional data in turn is used via automated systems to specifically machine an appropriate and idealized implant.

In some embodiments, such three-dimensional data in turn is used to facilitate selection of an implant from a variety of standard implants of varying dimensions and topographies, to promote selection of a best choice for implant from among a series of available implants.

In some embodiments, in either case, whereby a truly optimized implant is specifically and in a custom manner machined to ideally fit a subject, or an optimized implant reflective of a best fit from a wide variety of standards is chosen, the implant may further contain tapered sides as herein described and/or a rounded surface, as herein described, while ensuring the implantation height is about 2 mm below the articular cartilage layer of tissue proximal to the implantation site.

In some embodiments, the methods of this invention lend themselves to use of an automated system.

In some aspects, such automated systems are suitable for robotic assemblies to produce desired movements of surgical site preparation and implantation.

In some aspects, such automated systems are suitable for robotic assemblies to produce desired movements of the tools for preparing in implantation site, and in some embodiments, for implanting a solid substrate as herein described.

In some aspects, such automated systems are well established and allow for greater precision and control during surgical implantation procedures and may be further combined with customized methods, implants and tools as herein described and as described in other patents/applications recited herein and fully incorporated by reference herein, to provide idealized implantations and optimal results in a subject in need of same.

In some embodiments, this invention provides solid substrates and tools for use with same, which in turn comprise/accommodate a surface characterized by a radius of curvature, which radius of curvature may in some embodiments, be substantially similar to a radius of curvature of a tissue surface to which a tool and/or solid substrate as herein described is being applied.

In some embodiments, such radius of curvature of a tool or solid substrate as herein described may vary along an X-axis of a surface plane of said tool or solid substrate.

It will be appreciated that reference to symmetry or asymmetry in the radius of curvature of a solid substrate and/or its inclusion in kits of this invention and/or use and/or methods implementing same, may reflect a choice in approximating a curved tissue structure that the solid substrate and/kits containing same of this invention and/or use and/or methods implementing same is meant to address. In some aspects such choice is derived specifically from sagittal and/or coronal sections imaged of a defect site and the same dimensions and characteristics as determined from same will be applied to arrive at the most optimal implant/substrate.

In some aspects, the symmetry or asymmetry of the radius of curvature of a surface of a solid substrate of this invention or in a kit or for use and/or in accordance with a method of this invention will reflect sagittal and/or coronal variance of a comparable tissue site, as determined.

It will similarly be appreciated herein that reference to X- and/or Z-axes herein refers to sagittal and/or coronal planes and include consideration of same.

In some embodiments, such radius of curvature of a tool or solid substrate as herein described may vary along a Z-axis of a surface plane of said tool or solid substrate and in some embodiments, such radius of curvature of a tool or solid substrate as herein described may vary along both an X-axis and a Z-axis of a surface plane of said tool or solid substrate.

In some aspects, the radius of curvature of a tool and/or solid substrate as herein described comprising same is specifically customized to suit a defined radius of curvature along an X-axis or Z-axis or combination thereof of a surface of a tissue to which such tool or substrate is being applied, as derived from topology assessments conducted of the surface of the tissue.

In some embodiments, such radius of curvature of a tool or solid substrate as herein described may vary along a Z-axis of a surface plane of said tool or solid substrate and in some embodiments, such radius of curvature of a tool or solid substrate as herein described may vary along both an X-axis and a Z-axis of a surface plane of said tool or solid substrate.

In some aspects, the radius of curvature of a tool and/or solid substrate as herein described comprising same is specifically customized to suit a defined radius of curvature along an X-axis or Z-axis or combination thereof of a surface of a tissue to which such tool or substrate is being applied, as derived from topology assessments conducted of the surface of the tissue.

In some aspects, the tools for use with the implants/solid substrates and methods/uses of this invention include those as described in PCT International Patent Application Publication Number 2014/072982, fully incorporated by reference herein. In some aspects, such tools may be modified to in turn comprise/accommodate a surface characterized by a radius of curvature, which radius of curvature may in some embodiments, be substantially similar to a radius of curvature of a tissue surface to which a tool and/or solid substrate as herein described is being applied. In some aspects and referring to FIG. 1, the tools may comprise an implantation alignment tool 1-10 placed over the site of desired implantation, to promote insertion of a rod-like structure therethrough to within the tissue site of repair at an angle essentially 90 degrees/perpendicular to the tissue surface, which, in turn may attach to a drill and thereby be drilled into the underlying subchondral bone. A specialized drill, such as, for example, as described in WO 2014/072982, may be adapted to promote/facilitate rotation of a drill bit while placed over the rod-like structure but within the drill sleeve. A tissue reamer may be further applied and applied over the K-wire, and rotated to expand/enlarge the walls of the implantation site within the cartilage and subchondral bone. The tissue walls of the implant may be further processed, e.g. further smoothed using a tissue tapered shaper, which in turn may also insert over the rod-like structure, and rotated to smooth the tissue walls of the implantation site.

The tissue site may be shaped/smoothed/expanded or further shaped/smoothed/expanded with the aid of a cartilage cutter 1-120 or scalpel or other appropriate tool. The cartilage cutters of this invention comprise a head region and elongated body connected thereto, whereby the elongated body promotes proper grasping of the cartilage cutter tool.

In some embodiments, the cartilage cutter comprises:
an elongated handle;
a head region connected to said elongated handle, said head region further comprising
an apical portion which connects with said elongated handle;
a basal portion which inserts within an implantation site;
a first and second angled side regions, which taper from said apical portion toward said basal portion;
Wherein said first angled side region further comprises:
a tapered blade surface,
a supporting tapered angled surface positioned opposingly to said tapered blade surface; and
a hollowed region located therebetween,
whereby tissue in contact with said tapered blade surface cut thereby is of a thickness accommodating insertion within said hollowed region.

According to this aspect and in some embodiments, the basal surface is substantially flat. In some embodiments, the interior region between said first and second angled side regions is substantially hollowed, or in some embodiments, the interior region between said first and second angled side regions is substantially solid but contains a hollowed region into which the cut tissue may insert.

In some embodiments, the elongated handle has a grip surface and in some embodiments, the elongated handle is constructed to be ergonomic. In some embodiments, the elongated handle may be removably attached to said head region.

In some embodiments the head region is scalable to accommodate a range in dimensions of a tissue site where cartilage cutting is desired.

Thus FIGS. 1A-1S describe certain embodied methods and tools for preparing a tissue site for implantation in a site in need of osteochondral repair. Importantly, as noted in the methods as described herein, the tissue site preparation includes creating a smooth site of insertion promoting insertion of a therapeutic implant, which penetrates to the underlying bone.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment, the term "about" refers to a variance of from 1-10%, or in another embodiment, 5-15%, or in another embodiment, up to 10%, or in another embodiment, up to 25% variance from the indicated values, except where context indicates that the variance should not result in a value exceeding 100%.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

EXAMPLES

Example 1

Optimized Methods of Implantation of Solid Substrates

A variety of tools and implants are envisioned for use for implantation in osteochondral defects, and are to be considered as equivalents for use in the methods/processes of this invention.

A generalized procedure for preparing a defect site 1-05 is described by FIGS. 1A-1T. In this embodied process, an osteochondral defect in a condyle is treated. As a first step, a region in need of osteochondral repair is exposed, via conventional means. Prior to implantation of the osteochondral inductive implant, the implantation site is prepared. As a first matter, and as described in WO 2014/072982, fully incorporated by reference herein, an implantation alignment tool 1-10 is placed over the site of desired implantation, which tool promotes insertion of a rod-like structure, such as a k-wire 1-20, therethrough, for insertion within the tissue site of repair at an angle essentially 90 degrees/perpendicular to the tissue surface. FIG. 1B depicts the ability to attach the rod-like structure within a drill, for insertion in the lumen 1-40 of the implantation alignment tool (FIG. 1C). The rod-like structure is the drilled into the underlying subchondral bone 1-30 (FIG. 1D) and the alignment tool may contain markings 1-50 (FIG. 1E) serving as indicator for the depth at which the rod-like structure may be drilled/advanced therein.

Once the rod-like structure 1-20 is secured, the implantation alignment tool 1-10 may be removed, leaving the rod-like structure embedded through the cartilage and within the subchondral bone at the site of desired repair. For proper insertion of a therapeutic implant, the region of tissue into which an implant will be inserted needs to be vacated and appropriately prepared for insertion of an implant therein. Toward this end, the implantation site may be properly exposed via drilling/expanding the site for implant insertion.

FIG. 1G depicts placement of a drill sleeve 1-60 over the rod-like structure 1-20, with the sleeve potentially/optionally containing a terminus adapted to insert stably in the underlying tissue. A specialized drill, such as, for example, as described in WO 2014/072982, may be adapted to promote/facilitate rotation of a drill bit 1-70 while placed over the rod-like structure (FIG. 1H), but within the drill sleeve 1-60. The drill bit and drill sleeve are then removed (FIG. 1I), while the rod-like structure is maintained in place, embedded in the subchondral bone.

Thus, an expanded insert site is created/drilled in the underlying defect site through the cartilage and within the bone, creating an insertion region there through within the bone. While drilling alone may be sufficient, it is possible that additional processing/smoothing of the tissue circumference surrounding the implantation site is needed/desired. Toward this end, and also as described in WO 2014/072982, it may be desired to apply a tissue reamer 1-80 as depicted in FIGS. 1J-1M.

The reamer 1-80 is applied over the K-wire, as depicted in FIG. 1J and upon accommodation within the drilled exposed site of repair, the reamer may be rotated as depicted in FIG. 1K, with the terminal modifications of the reamer thereby expanding/enlarging the walls of the implantation site within the cartilage and subchondral bone. The reamer may further contain an indicator line 1-85, which provides a measure of depth for insertion and preparing of the tissue. For example, and as depicted in FIG. 1K when implanting within a central trochlear lesion, the indicator line reaches the articular surface level of the sulcus, for best insertion therein. Upon completion of the tissue modification, the reamer is removed (FIG. 1M) and the tissue site may be washed, e.g. with saline, via use of a syringe 1-100, as depicted in FIG. 1N.

The tissue walls of the implant may be further processed, e.g. further smoothed using a tissue tapered shaper 1-110, which in turn may also insert over the rod-like structure FIG. 1O. Similar to that achieved with the tissue reamer, rotation of the tissue shaper (FIG. 1P) may smooth the tissue walls of the implantation site, and the shaper may as well have an indicator line 1-115, to apprise the user of the appropriate depth for insertion (FIG. 1P). Upon completion of the tissue shaping, the shaper, as well may be removed from the site, as depicted in FIG. 1R.

The tissue site may again be washed, e.g. with saline, via use of a syringe 1-100, as depicted in FIG. 1S and the tissue site may be shaped/smoothed/expanded or further shaped/smoothed/expanded with the aid of the cartilage cutter 1-120 as depicted in FIG. 1T, or in some embodiments, with the aid of a scalpel or other appropriate tool.

Thus FIGS. 1A-1T describe certain embodied methods and tools for preparing a tissue site for implantation in a site in need of osteochondral repair. Importantly, as noted in the methods as described herein, the tissue site preparation includes creating a smooth site of insertion promoting insertion of a therapeutic implant, which penetrates to the underlying bone.

It will be appreciated that any of the tools may be so constructed to allow for a common handle to attach to the tool, for example, being adapted for a screw in or snap connection. In some aspects, such handle may be of ergonomic design to promote ideal manipulation of the tool.

FIGS. 5A-5E show an enlarged view and highlight additional features of the cartilage cutter 1-120 depicted in FIG. 1S. The cartilage cutter 5-120 contains an elongated body comprising a handle portion 5-230 and a head portion 5-220. In some aspects the cutter handle may comprise a rough surface (knerling) to prevent slipping of the fingers when grasping the tool. The skilled artisan will appreciate that any appropriate material may be used in the construction of the elongate body and/or hand portion of the device.

The cartilage cutter 5-120 head portion 5-220 is so constructed to provide an angled insertion region facilitating insertion of the head within the implantation site (FIGS. 5A-5I). The head portion 5-220 is further adapted to contain a blade edge 5-250, which as the cutter is rotated within the site, promotes the ability to trim the cartilage around the circumference of the hole/implantation site created. This ensures that any cartilage remnants protruding in the implantation site can be cut away with a safe and precision tool. The head region containing the blade edge 5-250 is so constructed to contain a region wherein the cut cartilage can insert therethrough 5-240 during cutting. Essentially the width between supporting part 5-260 and the blade edge 5-250 provides a hollowed groove through which the cut cartilage can insert 5-240 and be advanced as trimming is accomplished, in some embodiments circumferentially. The supporting part 5-260 is positioned opposingly to said blade edge 5-250, as is evident in FIGS. 5B, 5E, etc.

An second tapered surface 5-270 is shown, which may in some embodiments be smooth to ensure smooth trimming as the tool is rotated in the implantation site, and angled comparably to the blade-containing part angle.

In some aspects the second tapered surface 5-270 is flat but this is optional. The second tapered surface and overall dimensions and geometry of the cartilage cutter are so chosen/constructed to ensure ideal positioning of the cutter so that the blade surface is best positioned to trim the circumference of the implantation site for ideal insertion of the implant.

Figure 5A:
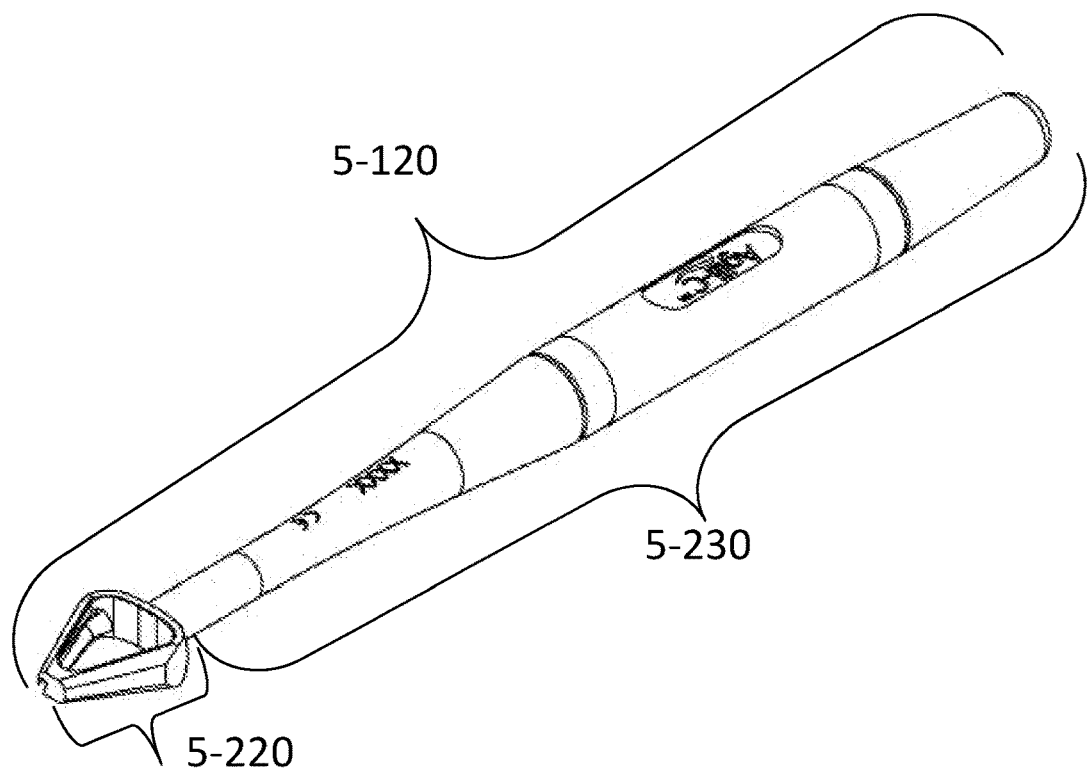
Figure 5B:
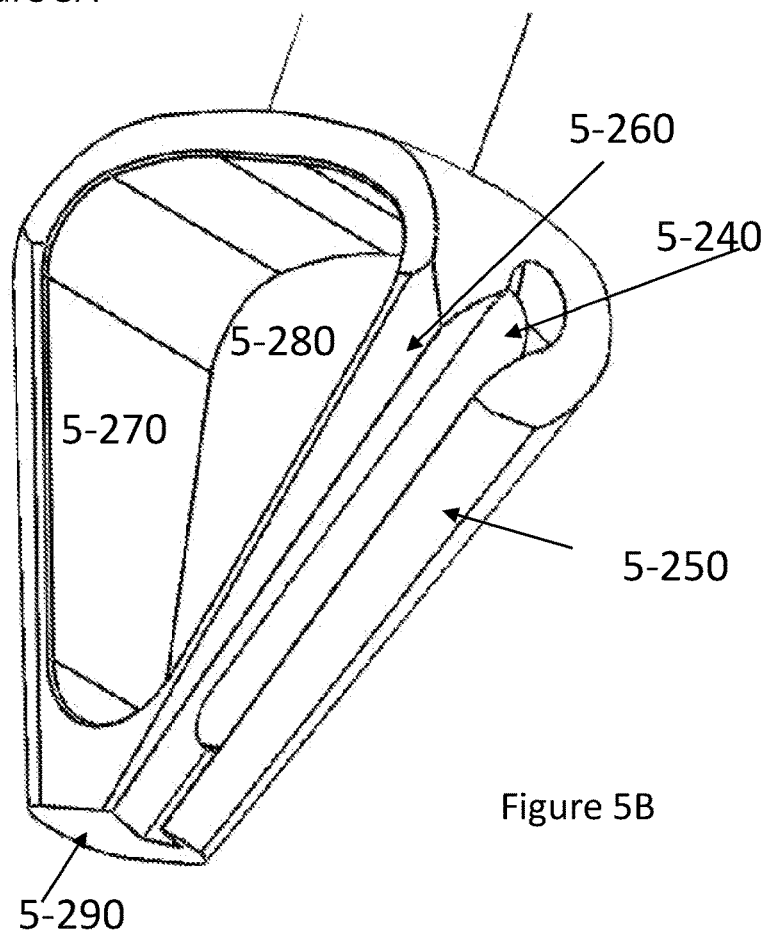

In some aspects, the interior 5-280 of the cartilage cutter is hollowed and in some aspects the interior 5-280 is filled. In some embodiments, the hollowed interior 5-280 facilitates easier and cleaner trimming of the cartilage, which may rotatingly insert therein during use. In some embodiments, the hollowed interior 5-280 facilitates ease of visualization of the implantation site on all sides during the trimming process (See FIG. 5B, and a rotated view of FIG. 5B presented in FIG. 5E).

The cutter head 5-220 may be so adapted to accommodate replaceable blade-containing parts, or in some embodiments, the cutter head itself 5-220 may be replaceable (FIG. 5F). Referring to FIG. 5C and FIG. 5D, the cutter head 5-220 may be adapted so that a blade-containing edge 5-250 part assembles onto the cutter head 5-220, to add the blade surface 5-250 whereas the head portion connected to the handle portion 5-230 contains the opposing supporting surface 5-260 and groove 5-240 into which the trimmed cartilage inserts, and the second tapered edge 5-270 may snap onto a similar tapered edge on the cutter head 5-220, so that only the blade containing part is replaced, exchanged. It will be apparent to the skilled artisan that other means of blade-edge specific replacement are considered, for example, similar to blade exchange on scalpel handles, and other configurations, as well.

In some aspects, the cutter head 5-220 is attachable to the cutter handles 5-230, for example as depicted in FIG. 5F, and any connecting system, e.g. snap connectors, screw-type arrangement and others is envisioned.

Figure 5G:
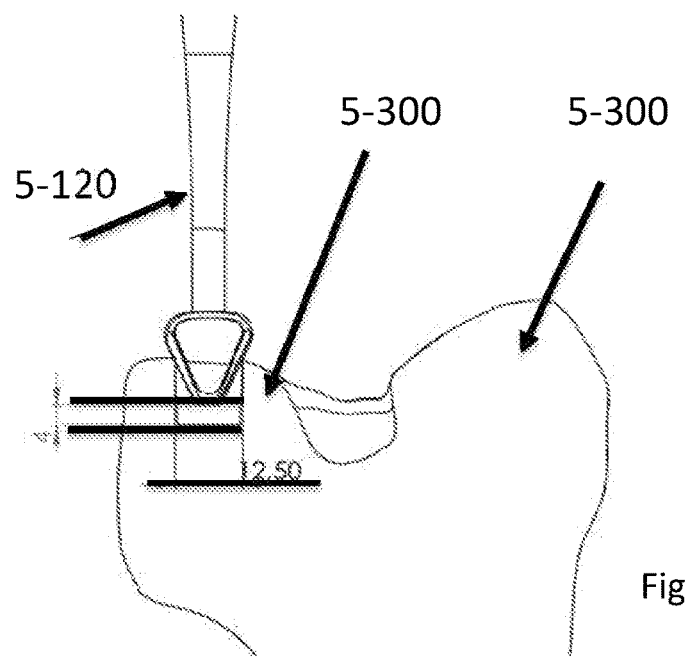
Figure 5H:
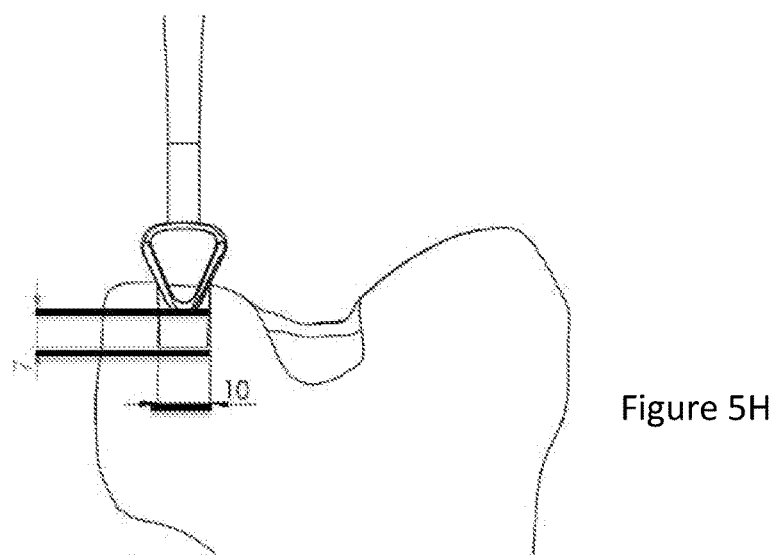
Figure 5I:
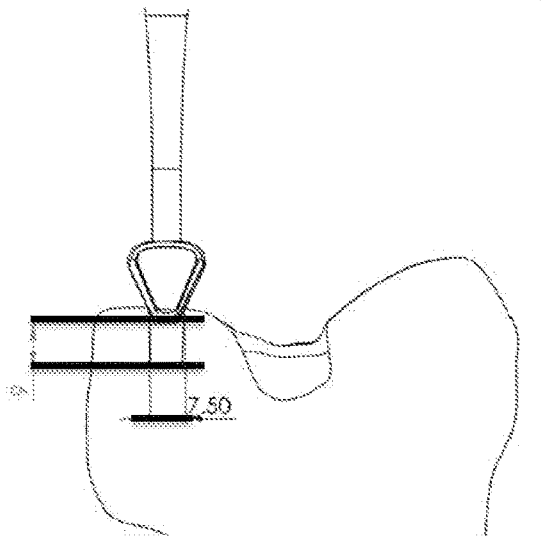

FIGS. 5G 5I depict various implantation sites, which may vary in size, for example, in terms of the depth and width of same and that the cartilage cutter 5-120, and in particular the dimensions of the cartilage cutter head portion 5-220 may be varied/adjusted in terms of overall size to suit application to a given implantation site, for optimal trimming of the cartilage.

FIGS. 2A-2D depict first introduction of an implant in a site in need of osteochondral repair, or bone repair or cartilage repair.

The implant 2-130 may be inserted in the prepared tissue site manually, as depicted in FIG. 2B, pressed to fit therein as depicted in FIG. 2C so that the implant is initially introduced/placed within the site of repair as depicted in FIG. 2D, where an upper boundary of the implant is essentially flush with or slightly raised above the articular cartilage surface.

While any appropriate implant for same is envisioned for use, in this embodied aspect, the implant as described in WO 2016/178226 is considered for use, in particular. The tools for use in preparing the site for implantation, as well, as described in WO 2016/178226 may be used to prepare the site for implantation, but in accordance with the methods of this invention, care is taken to ensure that site preparation includes the ability to implant a therapeutic solid substrate within a site of repair, whereby the implant apically abuts or reaches the tide mark, as herein described.

Similarly, any therapeutic implant is envisioned for use, for example, as described in U.S. Pat. No. 8,932,581 or 8,808,725, or 8,790,681 or WO 2014/125478, all of which are hereby incorporated by reference in their entirety.

A tamper 2-140 such as depicted in FIGS. 2E and 2F may be further used which tamper contains modified termini 2-150 that when used to further advance the implant in the site of desired repair, mitigate any damage to the implant. For example, the termini may be comprised of a durable silicon, such that same provides a non-stick, protective surface when applied to the implant, whereby applying force to the tamper 2-170 to further advance the implant in a press fit manner, such as that depicted in FIG. 2H facilitates implant insertion to the bone in the defect site, where the upper boundary of the implant is no longer flush with the articular cartilage layer, but instead is approximately 2 mm below the articular cartilage surface.

Furthermore the methods include when more than one therapeutic implant is being introduced that each implant is similarly implanted reaching the bone in each repair site, and being advanced such that the upper boundary of each implant is approximately 2 mm below the articular cartilage layer surface at each respective defect site. The two implants, in this circumstance should not abut each other, and instead an approximate 5 mm tissue distance between implant boundary sites should be preserved, as depicted in FIG. 2I.

FIG. 2J depicts another embodied aspect of the optimized method whereby the upper boundary of the therapeutic implant is approximately 2 mm below the articular cartilage surface in the defect site and a biocompatible/therapeutic polymer composition may be applied to the apex of the implant, as depicted in FIG. 2J. For example, a hyaluronic acid solution or hyaluronic acid hydrogel may be applied to the site 2-160 with a syringe 2-170, so that as depicted in FIG. 2K, the cartilage layer has a narrow, approximately 2 mm region 2-180 which is not filled in by the implant. FIG. 2L shows a transverse section through the region in FIG. 2J, of implantation of the substrate in underlying bone 2-210 and that the implant spans apically to a region about 2 mm lower 2-230 than the articular cartilage surface layer 2-220.

Example 2

Improved Solid Substrate Incorporation as a Function of Positioning of a Coralline-Based Solid Substrate Per the Methods of this Invention Coral plugs were prepared as described in PCT International Patent Application Publication Number WO2010058400 and implants were introduced into defect sites prepared as described in same.

Patients were evaluated at 6, 12, 18 and 24 months post-implantation and assessed for their pain level, function, daily activities (ADL), quality of life (QOL), involvement/ ease of participating in sports, using validated questioners Knee injury and Osteoarthritis Outcome Score (KOOS) and International Knee Documentation Committee (IKDC) (0=worse, 100=best). Additionally MRI and X-ray images were taken to evaluate the repaired tissue in terms of quality and overall appearance.

FIG. 3A taken at 3 months following implantation shows that the implant 3-10 was specifically positioned to be below the articular cartilage surface 3-200. The recess of the implant manifested as a region devoid of articular cartilage over the implant as depicted in the figure at void 3-210. Over time, cartilage regeneration occurs and the implant is being resorbed/resolved, as well. FIG. 3B shows that as early as 6 months post implantation, cartilage growth 3-200 over the implant region readily occurs. By 12 months post implantation, full thickness articular cartilage 3-200 has regenerated over the implant 3-10, which in turn is becoming fully integrated with underlying subchondral bone.

The images in FIG. 3 are representative and of the more than 200 patients in which coral based implants were provided via the method as described, remarkably in all cases, full thickness articular cartilage regeneration and resorption/incorporation of the implant in the underlying subchondral bone was seen.

To further highlight the unexpectedly improved outcome as a consequence of pursuit of the implantation procedures as described herein, pairwise comparisons of patients operated on at the same hospital at around the same time were conducted.

FIG. 4A-4H provides a representative comparison. Two male patients of similar age exhibiting similar cartilage defects, having previous ligament repair (ACL) were treated with implants of the same size (10 mm into the left knee, lateral condyle in the first patient, medial condyle in the second patient). The clinical outcome of both patients was excellent, in that both patients were completely pain free at 2 years and able to perform all activities, including strenuous sport activity.

Excellent cartilage repair was noted in both cases. Nonetheless, the patient in which the implant was specifically inserted to span through bone and into the cartilage layer, yet below the articular cartilage surface demonstrated superior cartilage thickness upon repair and formation of a precise tidemark between the regenerated cartilage and the regenerated bone. FIGS. 4A-4D depict images of the patients progress, following implantation of an implant as described herein. FIG. 4A is a photograph of the implantation site, whereby the implant (4-10) spanned through bone and cartilage, filling the tissue implantation site and being placed flush with the articular cartilage surface (4-200). FIG. 4B is an X-ray of the implantation site following implantation, whereby the implant 4-10 most apically spans beyond the tidemark, to the level of the articular surface 4-200. MRI images taken 2 years post implantation at lower (FIG. 4C) and higher (FIG. 4D) magnification demonstrate a reconstruction of the articular surface 4-195 and repaired cartilage similar to native cartilage in signal, however, the repaired cartilage proximal to the implantation site is thinner than native cartilage and no reconstruction of the tidemark was evident.

The table below provides an assessment of the patient progress from baseline through 2 years post-implantation. [see www.aaos.org/uploadedFiles/PreProduction/Quality/Measures/IKDCEnglishUS.pdf; www.koos.nu/].

| Patient 1 | | | | | |
|---|---|---|---|---|---|
| | IKDC | Pain | ADL | Sport | QOL |
| Baseline | 57.45 | 61.1 | 86.76 | 60 | 50 |
| 6M | 60.92 | 91.67 | 92.65 | 0 | 50 |
| 12M | 79.31 | 91.7 | 98.5 | 75 | 68.8 |
| 18M | 94.25 | 100 | 100 | 100 | 87.5 |
| 24M | 96.55 | 100 | 100 | 100 | 87.5 |

As is evident from the table, the patient demonstrated full healing and functional return of quality of life as a result of the treatment.

FIGS. 4E-4H depict images of the patients progress, following implantation of an implant as described herein, in accordance with embodied methods of this invention. FIG. 4E is a photograph of the implantation site, whereby the implant (4-10) spanned through bone and cartilage, filling the tissue implantation site and being placed 2 mm below the articular cartilage surface, at the level of the tidemark (4-200). FIG. 4F is an X-ray of the implantation site following implantation, whereby the implant 4-10 most apically is now flush with the tidemark 4-200. MRI images taken 2 years post implantation at lower (FIG. 4G) and higher (FIG. 4H) magnification demonstrate a reconstruction of the articular surface 4-195 and repaired cartilage similar to native cartilage in signal and in thickness, and full reconstruction of the tidemark was evident 4-200.

The table below provides an assessment of this patient's progress from baseline through 2 years post-implantation.

| Patient 2 | | | | | |
|---|---|---|---|---|---|
| | IKDC | Pain | ADL | Sport | QOL |
| Baseline | 37.93 | 69.4 | 75 | 50 | 31.3 |
| 6M | 79.31 | 100 | 100 | 75 | 81.3 |
| 12M | 75.86 | 97.2 | 97.1 | 85 | 87.5 |
| 18M | 85.06 | 100 | 100 | 90 | 87.5 |
| 24M | 90.8 | 100 | 100 | 100 | 100 |

Thus in methods of similar implantation, whereby the implant was essentially implanted flush with the articular cartilage surface, same provides for healing of the osteochondral defects in thus treated patients. Surprisingly, however, when the methods as embodied herein were pursued, the timing, quantity and quality of articular cartilage regeneration was dramatically improved in comparison to same, especially when evaluating the thickness of the regenerated cartilage and the formation of the tidemark It will be understood by those skilled in the art that various changes in form and details may be made therein without departing from the spirit and scope of the invention as set forth in the appended claims Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A method for implantation of a solid coralline-based substrate for promoting cell or tissue growth for the treatment of osteoarthritis, bone disorders, osteochondral defects, or cartilage lesions in a subject in need thereof, said method comprising:
   selecting and preparing a solid coralline-based substrate for promoting cell or tissue growth for stable implantation in a region traversing bone and cartilage in a subject, which solid coralline-based substrate has a length and width or that fits within the boundaries of the implantation site and is further characterized by a height such that when a first terminus of said solid coralline-based substrate is implanted within bone in a site for implantation, a second terminus of said solid coralline-based substrate is at a height at least 2 mm less than an articular cartilage layer surface or proximal to a tide mark region in said implantation site, wherein said solid coralline-based substrate comprises a coral or coral derivative; and
   implanting said selected and prepared solid coralline-based substrate within a site for implantation to span a basal to apical long axis of said site for implantation, wherein a first terminus of said implant is implanted within bone at the basal surface and a second terminus is oriented apically such that said second terminus is at a height at least 2 mm less than an articular cartilage layer surface or is proximal to a tide mark region in said implantation site such that a void is formed between an apical surface of said substrate and an articular cartilage layer to permit cell or tissue growth within the void subsequent to implanting said selected and prepared solid coralline-based substrate within the site; wherein said site of implantation has been prepared for insertion of said solid coralline-based substrate by creating a void of desired dimensions in terms of depth, length and width, and the side walls of the site for implantation have been created to contain a taper, and cartilage tissue within said site for implantation has been removed with the aid of a cartilage cutter, comprising:
   an elongated handle;
   a head region connected to said elongated handle, said head region further comprising an apical portion which connects with said elongated handle;
   a basal portion which inserts within an implantation site, the basal portion having a basal surface that is continuous and substantially flat;
   a first and second angled side regions, which taper from said apical portion toward said basal portion;
   wherein said first angled side region further comprises:
   a tapered blade surface,
   a supporting tapered angled surface positioned opposingly to said tapered blade surface; and
   a hollowed region located therebetween, whereby tissue in contact with said tapered blade surface cut thereby is of a thickness accommodating insertion within said hollowed region.

2. The method of claim 1, wherein said solid coralline-based substrate has a height of between 1-20 mm.

3. The method of claim 1, wherein said solid coralline-based substrate has a diameter of about 1-50 mm.

4. The method of claim 1, wherein said solid coralline-based substrate is further characterized by tapered sides.

5. The method of claim 4, wherein said solid coralline-based substrate is further characterized by comprising tapered sides at an angle of from 0.75 to about 4 degrees from a longitudinal axis along said solid coralline-based substrate.

6. The method of claim 5, wherein said tapered sides are at an angle of about two degrees from a longitudinal axis along said solid coralline-based substrate.

7. The method of claim 1, wherein said solid coralline-based substrate is characterized by a conical or pyramidal frustum.

8. The method of claim 1, wherein said solid coralline-based substrate consists essentially of aragonite, calcite, or a combination thereof.

9. The method of claim 8, wherein said solid coralline-based substrate is characterized by a specific fluid uptake capacity value of at least 75%.

10. The method of claim 9, wherein said establishing a specific fluid uptake capacity value of said solid coralline-based substrate comprises the step of contacting said solid coralline-based substrate with a fluid for from 0.1-15 minutes, allowing for spontaneous fluid uptake of said fluid within said solid coralline-based substrate to arrive at said spontaneous fluid uptake value.

11. The method of claim 9, wherein establishing said specific fluid uptake capacity value of said solid coralline-based substrate further comprises the step of contacting said solid coralline-based substrate with a fluid and applying negative pressure to said solid coralline-based substrate to promote maximal uptake of said fluid within said solid coralline-based substrate to arrive at a total fluid uptake value.

12. The method of claim 9, wherein said fluid is a biologic fluid or a blood analog or a synthetic blood analog.

13. The method of claim 9, wherein said fluid is water.

14. The method of claim 8, wherein said solid coralline-based substrate is isolated from enriched coral that has been chemically modified to incorporate silicium into the solid coralline-based substrate.

15. The method of claim 1, wherein said solid coralline-based substrate comprises a hollow or hollows along a Cartesian coordinate axis of said solid coralline-based substrate.

16. The method of claim 15, wherein said hollow or hollows are along an axis substantially spanning from said second terminus toward said first terminus.

17. The method of claim 15, wherein said hollow or hollows are along an axis extending from said second terminus up to half the height of said solid coralline-based substrate, toward said first terminus.

18. The method of claim 15, wherein said hollow or hollows are along an axis extending from said second terminus up to 30% of the height of said solid coralline-based substrate, toward said first terminus.

19. The method of claim 1, wherein said solid coralline-based substrate has an overall shape that is ovoid or ellipsoid.

20. The method of claim 1, wherein said solid coralline-based substrate comprises an oval contour.

21. The method of claim 1, wherein said implanting is conducted at an implant angle of from about 0.75 to about 4 degrees from an axis perpendicular to the surface of the tissue site being thus treated.

22. The method of claim 21, wherein said implanting is conducted at an implant angle of from about 2 degrees from an axis perpendicular to the surface of the tissue site being thus treated.

23. The method of claim 1, wherein said method further comprises the step of contacting said solid coralline-based substrate with cells or tissue or tissue derivatives or blood or blood derivatives pre-operative, intra-operative or post-operative.

24. The method of claim 1, wherein said solid coralline-based substrate promotes cell or tissue growth in tissue of a subject afflicted with a defect or disorder or disease of the cartilage or bone or a combination thereof.

25. The method of claim 24, wherein said cartilage defect or disorder or disease comprises a full or partial thickness articular cartilage defect; osteochondral defect; osteoarthritis, avascular necrosis; osteochondritis dissecans; bone cyst, non-union fractures, fracture, bone defect, bone edema, osteoporosis, a joint defect or a defect resulting from trauma, sports, or repetitive stress.

26. The method of claim 25, wherein said method serves to delay or eliminate the need for full or partial joint replacement in an affected subject.

27. The method of claim 26, wherein said method serves to resurface an affected joint in a subject.

28. The method of claim 1, wherein said method may be accomplished via automated systems for both preparation and implantation of said solid coralline-based substrate.

29. The method of claim 28, wherein said automated system may make use of robotic systems.

30. The method of claim 1, wherein said method may provide a customized implant and implantation based on pre-operative imaging and intra-operative findings.

31. The method of claim 1, further comprising: applying a biocompatible polymer layer or hydrogel or therapeutic compound or cell population or combination thereof, to an apical surface of said implant to fill said void formed between said second terminus and said articular cartilage layer surface.

* * * * *